(12) United States Patent  (10) Patent No.: US 9,056,851 B2
Tonge et al.  (45) Date of Patent: Jun. 16, 2015

(54) THIOLACTONE ANTIBIOTICS

(75) Inventors: Peter Tonge, Setauket, NY (US); Carl Machutta, Boyertown, PA (US); Gopal Reddy Bommineni, Port Jefferson, NY (US); Kanishk Kapilashrami, Stony Brook, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/007,265

(22) PCT Filed: Mar. 23, 2012

(86) PCT No.: PCT/US2012/030354
§ 371 (c)(1),
(2), (4) Date: Dec. 11, 2013

(87) PCT Pub. No.: WO2012/135027
PCT Pub. Date: Oct. 4, 2012

(65) Prior Publication Data
US 2014/0113941 A1   Apr. 24, 2014

Related U.S. Application Data

(60) Provisional application No. 61/467,761, filed on Mar. 25, 2011.

(51) Int. Cl.
*A61K 31/381* (2006.01)
*C07D 333/32* (2006.01)
*C07D 409/06* (2006.01)
*C07D 409/12* (2006.01)

(52) U.S. Cl.
CPC ............ *C07D 333/32* (2013.01); *C07D 409/06* (2013.01); *C07D 409/12* (2013.01); *A61K 31/381* (2013.01)

(58) Field of Classification Search
CPC ............................ C07D 333/32; A61K 31/381
USPC .............................................. 514/445; 549/64
See application file for complete search history.

(56) References Cited

U.S. PATENT DOCUMENTS

| 7,649,012 B2 | 1/2010 | Kuhajda et al. |
| 2003/0158153 A1 | 8/2003 | Menta et al. |
| 2003/0171420 A1 | 9/2003 | Berry et al. |

OTHER PUBLICATIONS

Dormann, 2007, Angewandte Chemie, vol. 46, Issue 7, p. 1160-1163.*
Toyama, 2006, Tetrahedron Letters, vol. 47, Issue 49, p. 8793.*
Sakya, 2001, Bioorganic & Medicinal Chemistry Letters, vol. 11, Issue 20, p. 2751-2754.*
Kikionis et al. (2009). Regioselective ring opening of thiomalic acid anhydrides by carbon nucleophiles. Synthesis and X-ray structure elucidation of novel thiophenone derivatives. *Tetrahedron*, 65(18), 3711-3716.
Notification of Transmittal of the International Search Report and the Written Opinion of the International Searching Authority, or the Declaration, including an International Search Report and Written Opinion of the International Searching Authority, mailed Oct. 23, 2012 in connection with PCT International Application No. PCT/US2012/030354, filed Mar. 23, 2012.
Notification Concerning Transmittal of International Preliminary Report on Patentability (Chapter I of the Patent Cooperation Treaty), including an International Preliminary Report on Patentability and Written Opinion of the International Searching Authority, mailed Oct. 10, 2013 by The International Bureau of WIPO in connection with PCT International Application No. PCT/US2012/030354, filed Mar. 23, 2012.

* cited by examiner

*Primary Examiner* — Rebecca Anderson
*Assistant Examiner* — Karen Cheng
(74) *Attorney, Agent, or Firm* — Gary J. Gershik; Cooper & Dunham LLP

(57) ABSTRACT

This invention provides a compound having the structure

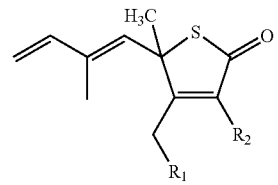

wherein $R_1$ is H,

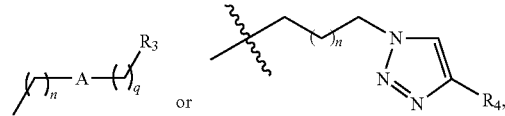

wherein
n and q are independently an integer from 0 to 8;
A is absent or present and when present is -continued

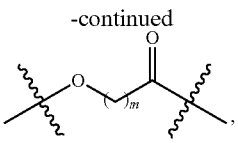

wherein m is an integer from 0 to 8;

R₃ is an amino, alkyl, aryl, heteroaryl, diol, piperazine, morpholine, piperidine, triazole, azide or biphenyl, each with or without substitution, branched or unbranched, or

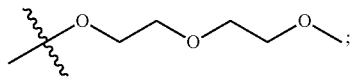 [SMILES: *OCCOCCOC]

and

R₄ is alkyl, aryl, or heteroaryl, each with or without substitution, branched or unbranched, R₂ is H, CH₃, or alkyl, aryl, heteroaryl, pyrrole, diazole, or triazole, each with or without substitution, branched or unbranched, or

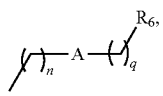

wherein n and q are independently an integer from 0 to 8;

A is absent or present and when present is

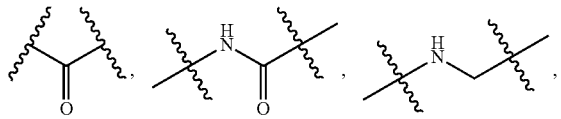

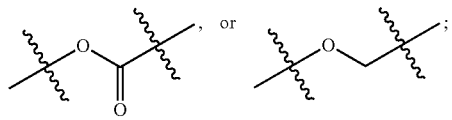

and

R₆ is azide, methoxy, trifluoromethyl, biphenyl, substituted phenyl, substituted triazole, or alkyl, aryl or heteroaryl, with or without substitution, branched or unbranched, when R₁ is H then R₂ is other than H or CH₃, and when R₂ is H or CH₃ then R₁ is other than H, or a pharmaceutically acceptable salt thereof.

31 Claims, 9 Drawing Sheets

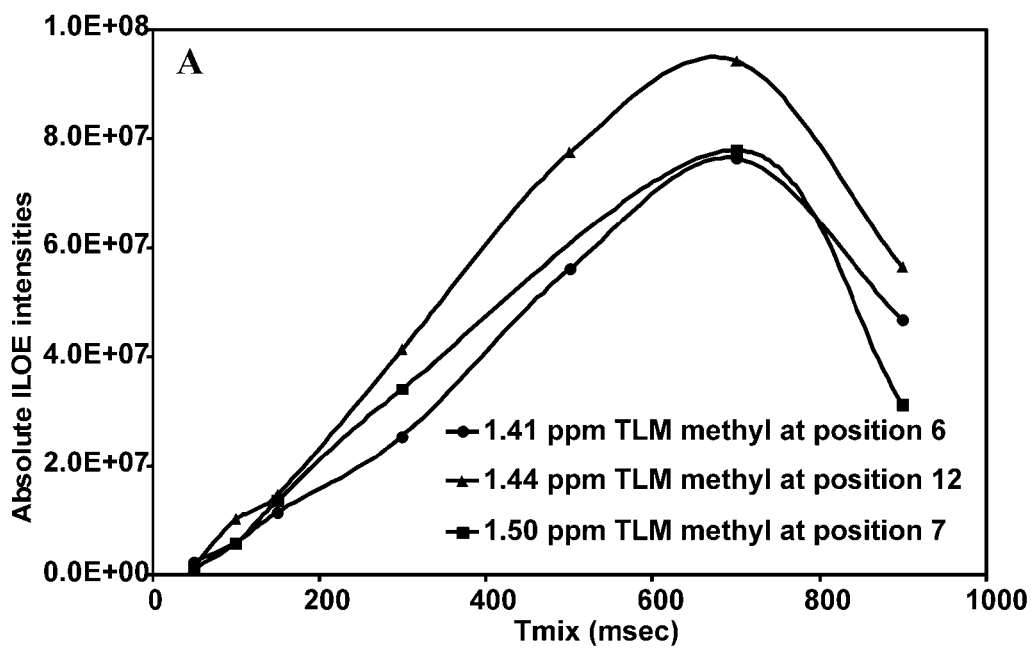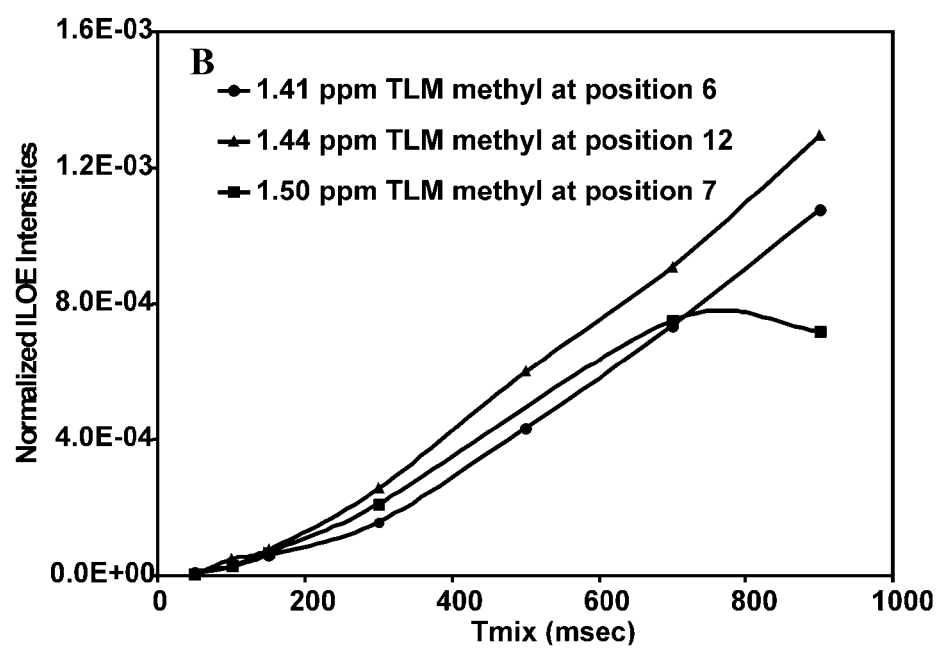
Figure 7

THIOLACTONE ANTIBIOTICS

This application is a §371 national stage of PCT International Application No. PCT/US2012/030354, filed Mar. 23, 2012, claiming the benefit of U.S. Provisional Application No. 61/467,761, filed Mar. 25, 2011, the contents of each of which are hereby incorporated by reference in their entirety.

The invention was made with government support under NIH Grant number 5R01AI04463909 awarded by the National Institutes of Health. The government may have certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Thiolactomycin (TLM) is a natural product thiolactone first isolated from *Nocardia* sp., a bacterial strain identified from a Japanese soil sample in 1981 (4). TLM is rapidly absorbed in rats when administered both orally and by intramuscular injection, and it provides protection from both urinary tract and oral infections in animals infected with *Serratia marcescens* and *Klebsiella pneumoniae* (14).

The antibacterial activity of TLM is known to result from an inhibition of fatty acid biosynthesis. TLM is a selective and reversible inhibitor of the KAS enzymes in the FAS-II pathway (4, 6, 16), but does not inhibit the mammalian FAS-I enzymes (17). TLM resistant *E. coli* strains contain mutations in the fabB KAS gene (18) and overproduction of FabB confers TLM resistance in vivo (19) suggesting that FabB is the major cellular target. Based on kinetic and structural data, TLM is thought to be a competitive inhibitor of malonyl-ACP (5-6), and studies have shown that TLM binds preferentially to the covalently modified KAS acyl-enzyme intermediate with slow onset kinetics (15).

Although slow onset kinetics are observed when TLM binds to acyl-KasA (15), the inhibitor only has a $K_i^*$ value of 2 μM for the C171Q acyl-enzyme mimic (7, 15). The properties of TLM have stimulated efforts aimed at making analogs with improved antibacterial activity of the compound. These studies have primarily concentrated on the 5 position of the TLM ring primarily due to ease of synthesis (20-24). However, these studies have failed to improve the activity of TLM. Described herein, is a new class of TLM analogue antibiotics.

SUMMARY OF THE INVENTION

This invention provides a compound having the structure

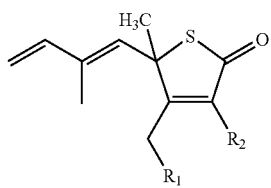

wherein $R_1$ is H,

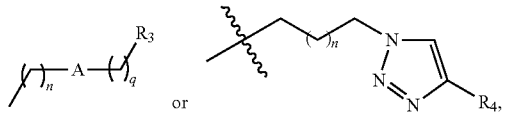

wherein n and q are independently an integer from 0 to 8;

A is absent or present and when present is

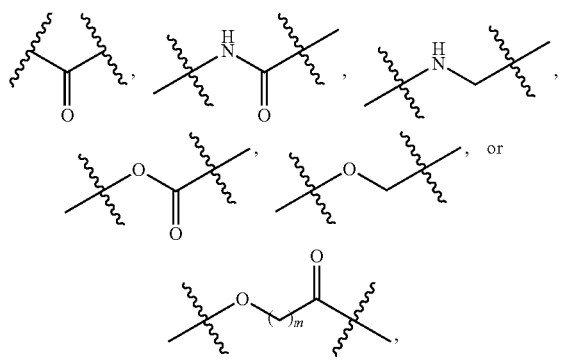

wherein m is an integer from 0 to 8;

$R_3$ is an amino, alkyl, aryl, heteroaryl, diol, piperazine, morpholine, piperidine, triazole, azide or biphenyl, each with or without substitution, branched or unbranched, or

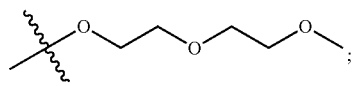 [SMILES: *OCCOCCOC]

and $R_4$ is alkyl, aryl, or heteroaryl, each with or without substitution, branched or unbranched, $R_2$ is H, $CH_3$, or alkyl, aryl, heteroaryl, pyrrole, diazole, or triazole, each with or without substitution, branched or unbranched, or

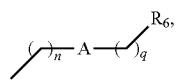

wherein n and q are independently an integer from 0 to 8;

A is absent or present and when present is

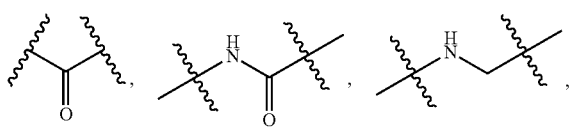

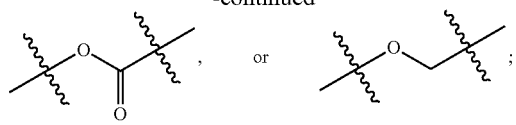

and

R$_6$ is azide, methoxy, trifluoromethyl, biphenyl, substituted phenyl, substituted triazole, or alkyl, aryl or heteroaryl, with or without substitution, branched or unbranched, when R$_1$ is H then R$_2$ is other than H or CH$_3$, and when R$_2$ is H or CH$_3$ then R$_1$ is other than H, or a pharmaceutically acceptable salt thereof.

BRIEF DESCRIPTION OF THE FIGURES

FIG. 7. Interligand NOE build up curves. A) NOE build up curves for the TLM methyls C6, C7 and C12 upon inversion of the PK940 methyl cluster at ~0.75 ppm are shown. The build-up rate for the TLM methyl 12 at 1.44 ppm (depicted as solid triangles) appear to be faster than the build-up's for 6 and 7 implying that methyl 12 may be closer the terminal PK940 C1' methyl. B) NOE build ups for TLM methyls 6, 7 and 12 normalized with respect to the inverted peak at ~0.75 ppm show the same extended utility of the longer mixing times for estimating distances with the limitations mentioned in the text.

DETAILED DESCRIPTION OF THE INVENTION

Figure 1:
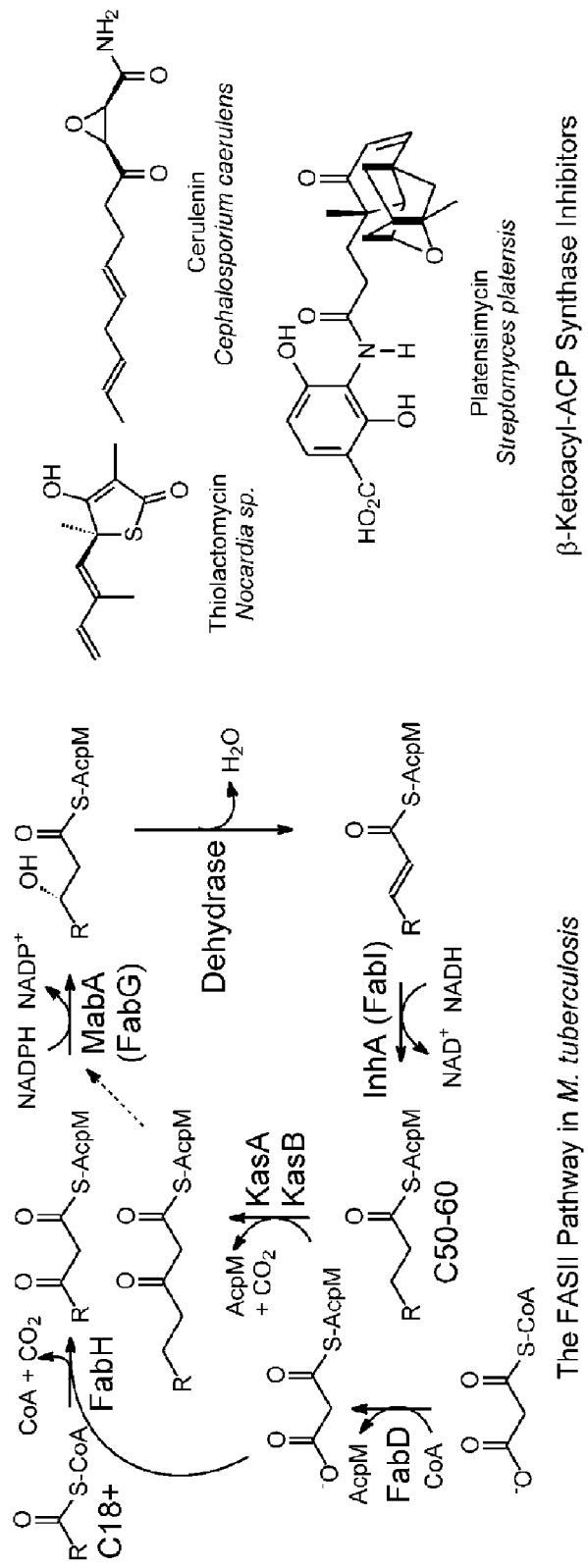
FIG. 1. The FAS-II Pathway in *M. tuberculosis* and natural product KAS inhibitors. Note KasA and KasB are the KASI and KASII enzymes in *M. tuberculosis*. In *E. coli* they are FabB and FabF. (KASI=KasA=FabB; KASII=KasB=FabF).

This invention provides compound having the structure

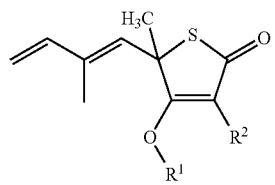

wherein R$_1$ is H,

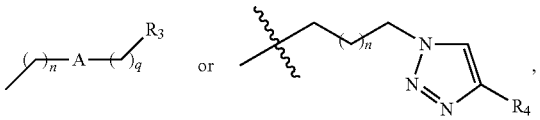

wherein
n and q are independently an integer from 0 to 8;
A is absent or present and when present is

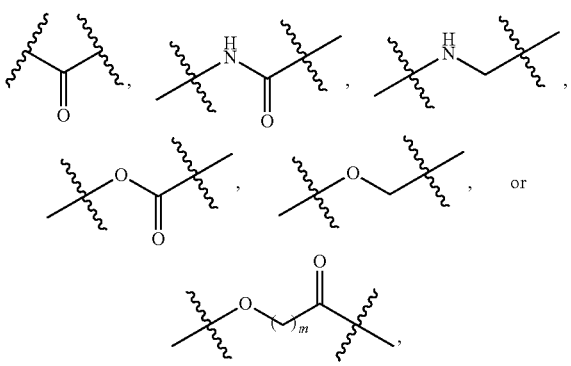

wherein m is an integer from 0 to 8;
R$_3$ is an amino, alkyl, aryl, heteroaryl, diol, piperazine, morpholine, piperidine, triazole, azide or biphenyl, each with or without substitution, branched or unbranched, or

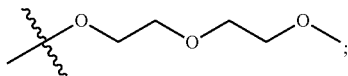

and
R$_4$ is alkyl, aryl, or heteroaryl, each with or without substitution, branched or unbranched,
R$_2$ is H, CH$_3$, or alkyl, aryl, heteroaryl, pyrrole, diazole, or triazole, each with or without substitution, branched or unbranched, or

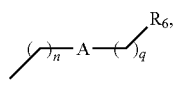

wherein
n and q are independently an integer from 0 to 8;
A is absent or present and when present is

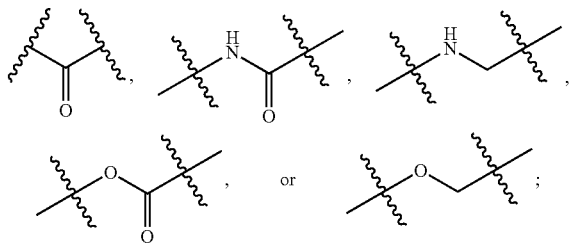

and
$R_6$ is azide, methoxy, trifluoromethyl, biphenyl, substituted phenyl, substituted triazole, or alkyl, aryl or heteroaryl, with or without substitution, branched or unbranched,
when $R_1$ is H then $R_2$ is other than H or $CH_3$, and when $R_2$ is H or $CH_3$ then $R_1$ is other than H,
or a pharmaceutically acceptable salt thereof.
This invention provides compound having the structure

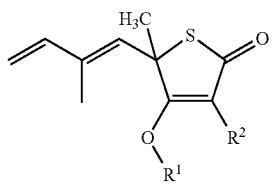

wherein $R_1$ is H,

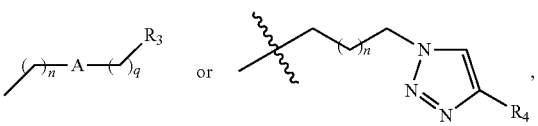

wherein
n and q are independently an integer from 0 to 8;
A is

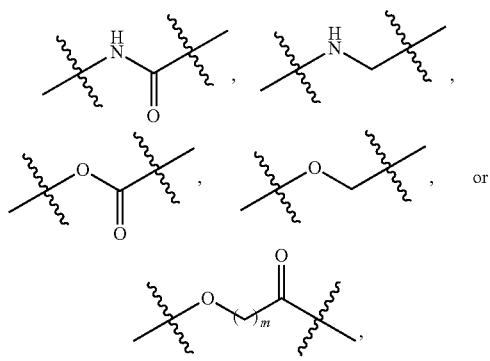

wherein m is an integer from 0 to 8;
$R_3$ is alkyl, aryl, heteroaryl, diol, piperazine, morpholine, piperidine, or biphenyl, each with or without substitution, branched or unbranched, or

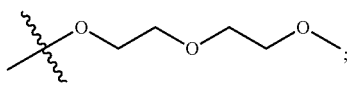 [SMILES: *OCCOCCOC]

and
$R_4$ is alkyl, aryl, or heteroaryl, each with or without substitution, branched or unbranched,
$R_2$ is H, $CH_3$, or alkyl, aryl, heteroaryl, pyrrole, diazole, or triazole, each with or without substitution, branched or unbranched, or

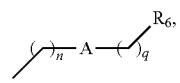

wherein
n and q are independently an integer from 0 to 8;
A is

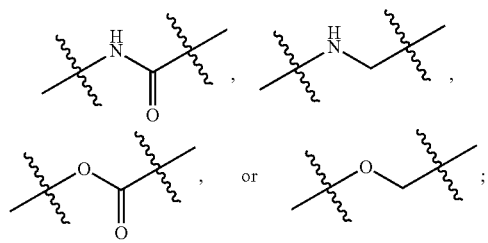

and
$R_6$ is alkyl, aryl or heteroaryl, with or without substitution, branched or unbranched,
when $R_1$ is H then $R_2$ is other than H or $CH_3$, and when $R_2$ is H or $CH_3$ then $R_1$ is other than H,
or a pharmaceutically acceptable salt thereof.
In some embodiments, $R_1$ is

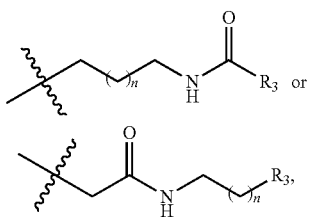

wherein
n and q are independently an integer from 0 to 8; and
$R_3$ is alkyl, aryl, heteroaryl, diol, piperazine, morpholine, piperidine, or biphenyl, each with or without substitution, branched or unbranched;
or a pharmaceutically acceptable salt thereof.
In some embodiments, $R_3$ is

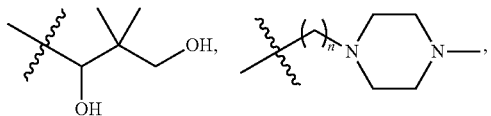

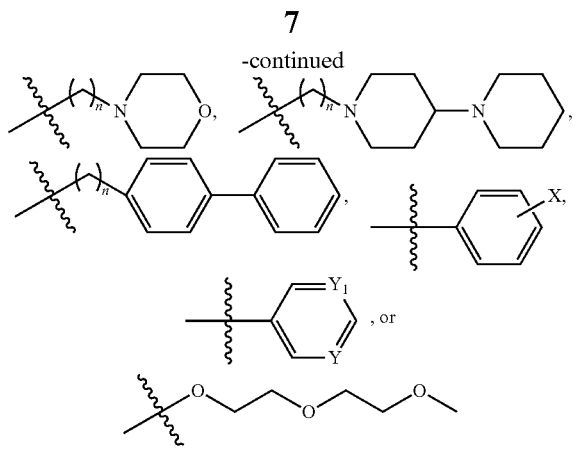
wherein
m is an integer from 0-8;
X is F, Cl, Br, phenyl, or $C_1$-$C_4$ alkyl;
Y is N or C; and
$Y_1$ is N or C,
or a pharmaceutically acceptable salt thereof.
In some embodiments, the compound has the structure
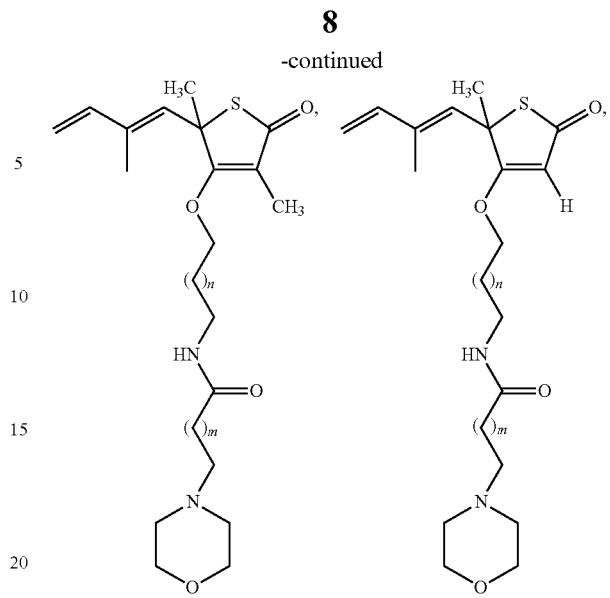
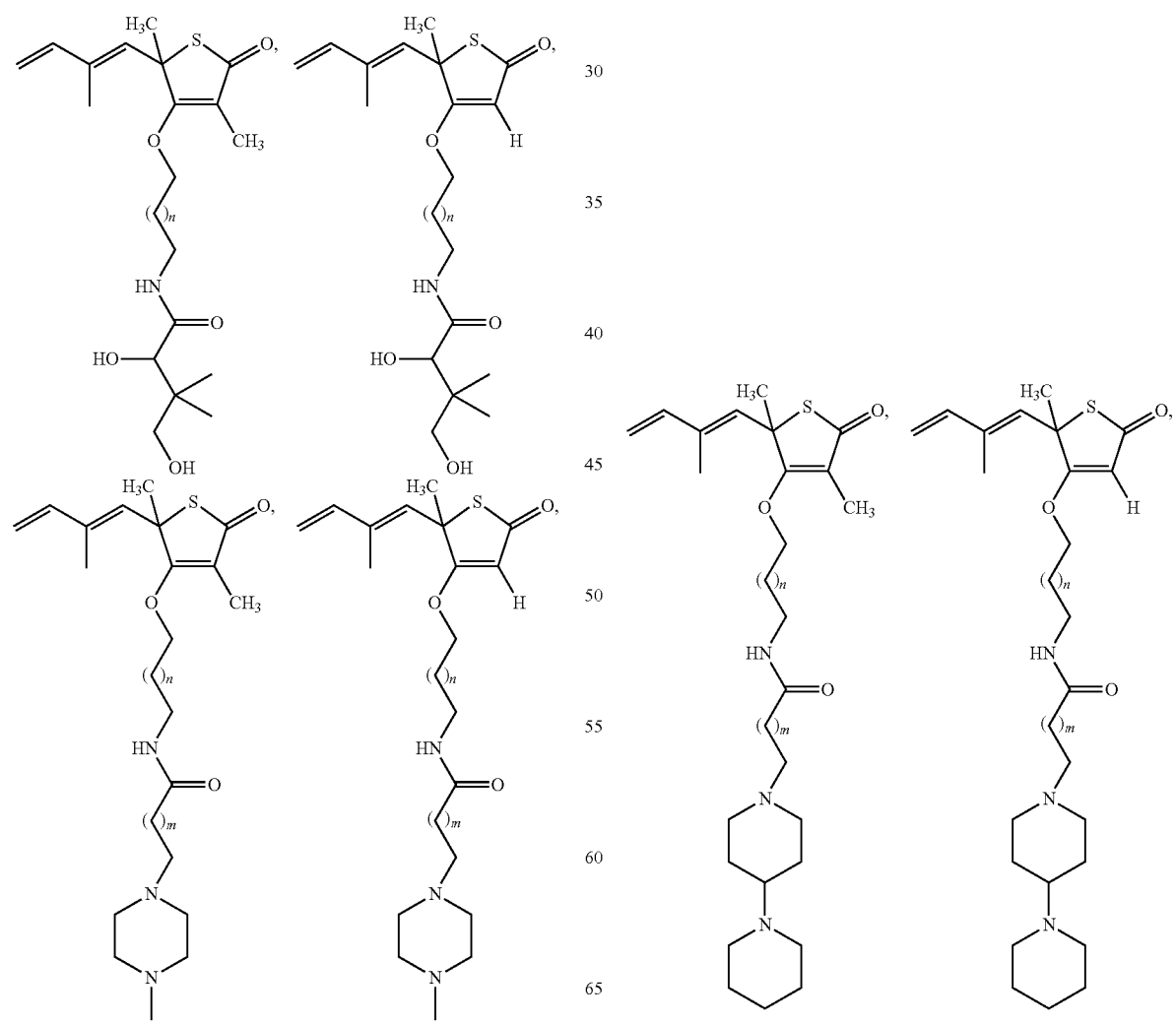

-continued

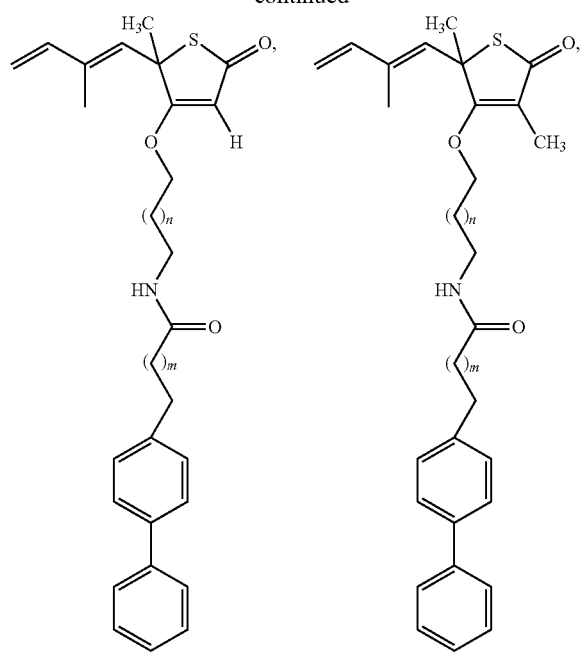

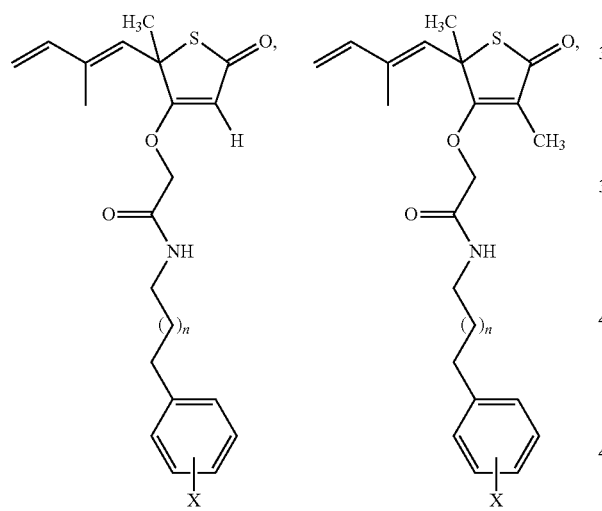

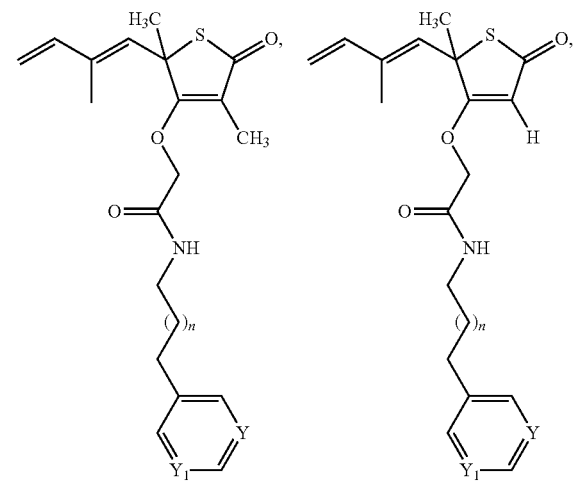

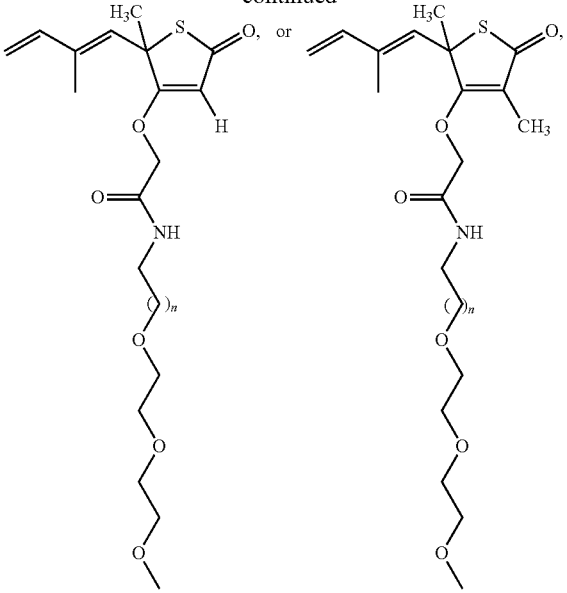

wherein
n and m are each independently an integer from 0 to 8;
X is F, Cl, Br, phenyl, or $C_1$-$C_4$ alkyl;
Y is N or C; and
$Y_1$ is N or C,
or a pharmaceutically acceptable salt thereof.

In some embodiments, $R_1$ is

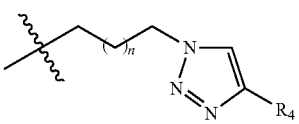

wherein
n is an integer from 0 to 8; and
$R_4$ is alkyl, aryl, or heteroaryl, each with or without substitution, branched or unbranched,
or a pharmaceutically acceptable salt thereof.

In some embodiments, the compound has the structure

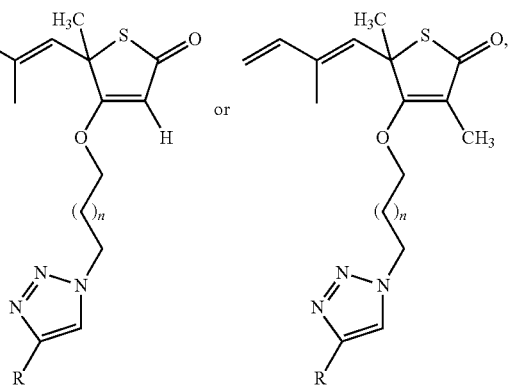

wherein
n is an integer from 0 to 8; and
$R_4$ is alkyl, aryl, or heteroaryl, each with or without substitution, branched or unbranched, or a pharmaceutically acceptable salt thereof.

In some embodiments, $R_2$ is

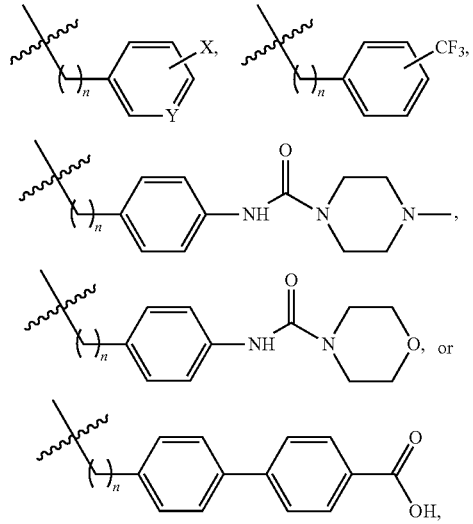

wherein n is an integer from 0-8;

X is H, Cl, F, Br, phenyl, $CO_2H$, or aryl or $C_1$-$C_4$ alkyl each with or without substitution, branched or unbranched; and Y is C, O, S, or N, or a pharmaceutically acceptable salt thereof.

In some embodiments, the compound has the structure

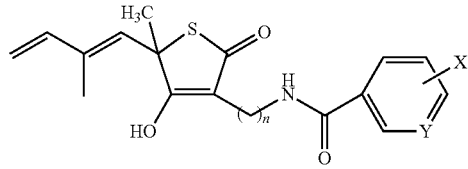

wherein n is an integer from 0-8;

X is F, Cl, Br, phenyl, or $CO_2H$; and

Y is N or C, or a pharmaceutically acceptable salt thereof.

In some embodiments, the compound has the structure

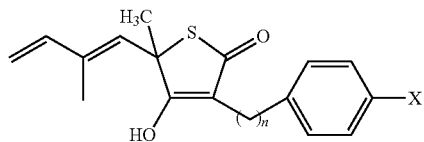

wherein n is an integer from 0-8;

X is F, Cl, Br, phenyl, or $CO_2H$; and

Y is N or C, or a pharmaceutically acceptable salt thereof.

In some embodiments, the compound has the structure

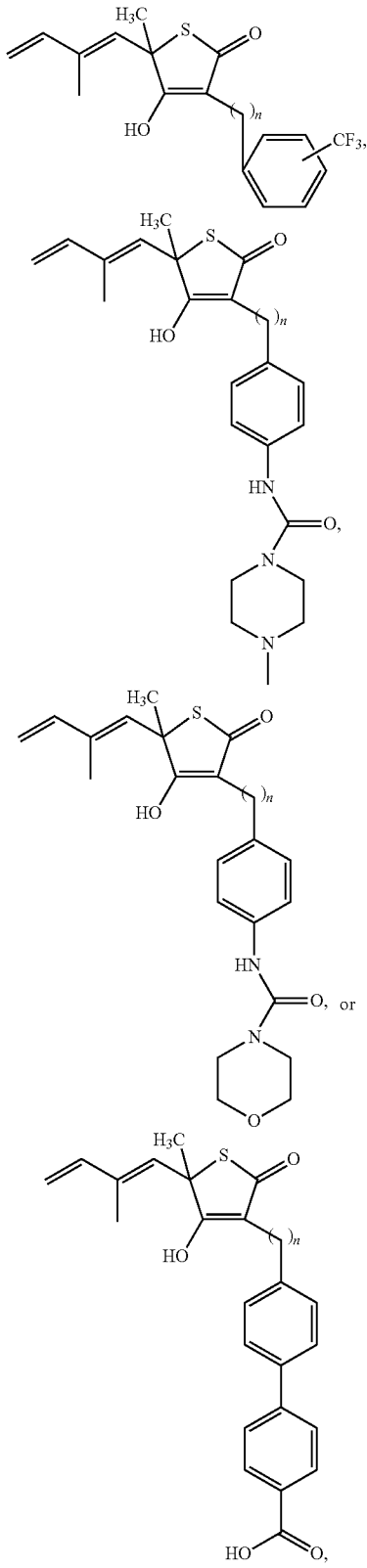

wherein n is an integer from 0 to 8, or a pharmaceutically acceptable salt thereof.

In some embodiments $R_2$ is

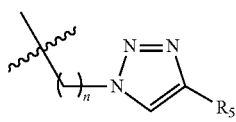

wherein
n is an integer from 0-8; and
$R_5$ is alkyl, aryl, or heteroaryl, each with or without substitution, branched or unbranched,
or a pharmaceutically acceptable salt thereof.
In some embodiments, the compound has the structure

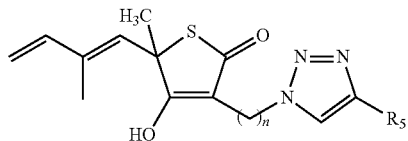

wherein
n is an integer from 0-8; and
$R_5$ is alkyl, aryl, or heteroaryl, each with or without substitution, branched or unbranched,
or a pharmaceutically acceptable salt thereof.
In some embodiments, $R_2$ is

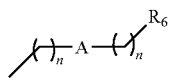

wherein
n and q are independently an integer from 0 to 8;
A is

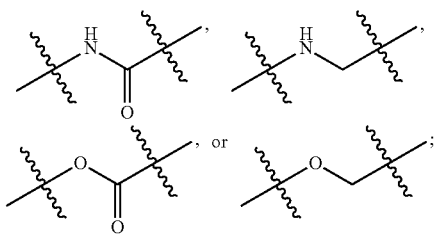

and
$R_6$ is alkyl, aryl or heteroaryl, with or without substitution, branched or unbranched,
or a pharmaceutically acceptable salt thereof.
In some embodiments, the compound has the structure

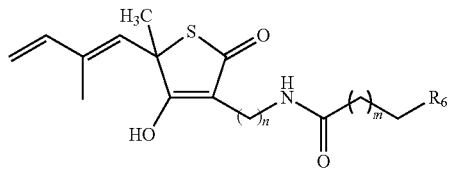

wherein
n and m are each independently an integer from 0 to 8; and
$R_6$ is alkyl, aryl or heteroaryl, each with or without substitution, branched or unbranched,
or a pharmaceutically acceptable salt thereof.
In some embodiments, $R_6$ is

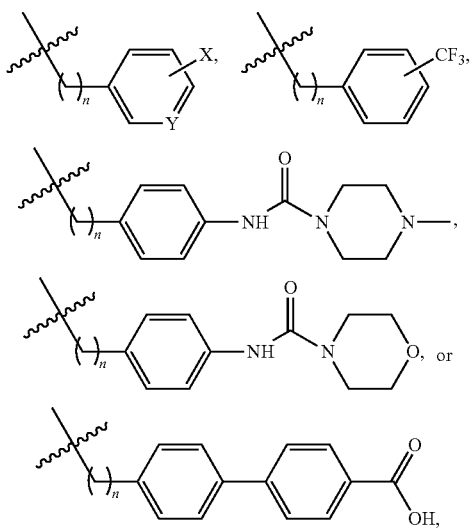

wherein
n is an integer from 0-8;
X is H, Cl, F, Br, phenyl, $CO_2H$, or aryl or $C_2$-$C_4$ alkyl each with or without substitution, branched or unbranched; and
Y is C, O, S, or N,
or a pharmaceutically acceptable salt thereof.
In some embodiments, $R_2$ is

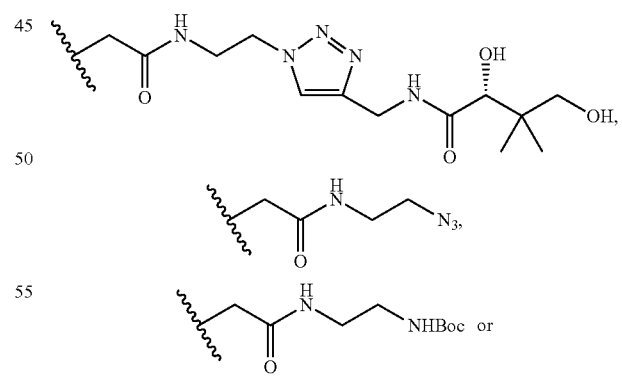

or a pharmaceutically acceptable salt thereof.

In some embodiments, $R_2$ is —$CH_2CH_3$, —$CH_2CH_2CH_3$,
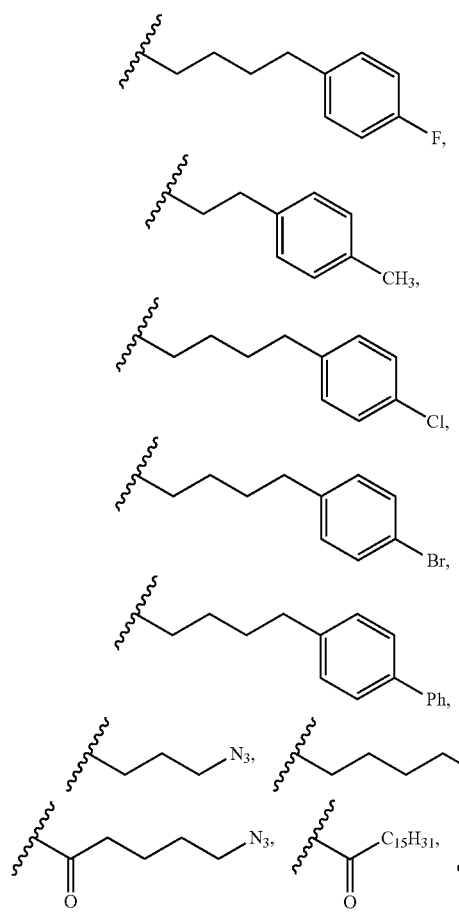
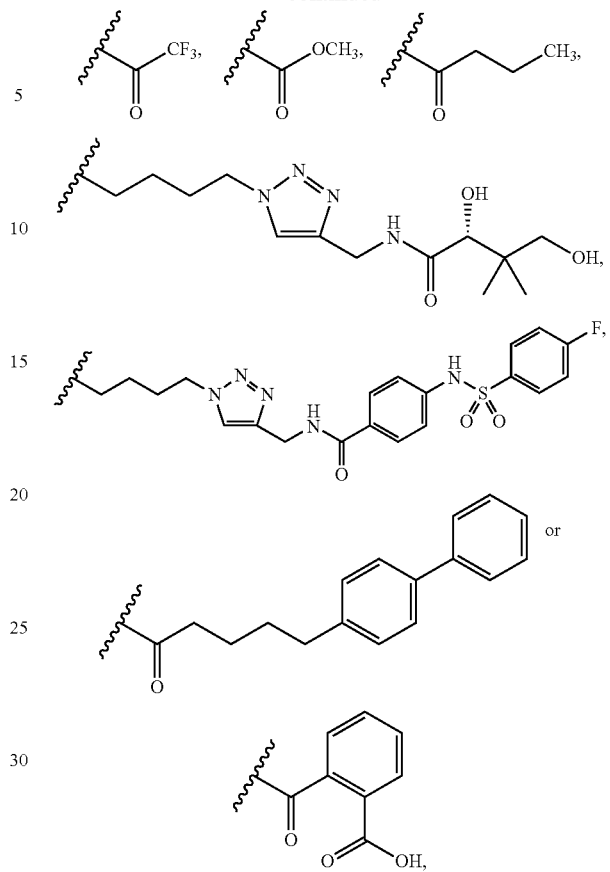
or a pharmaceutically acceptable salt thereof.
In some embodiments, the compound has the structure
| | |
|---|---|
| TLM | 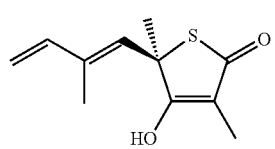 |
| TLM2 | 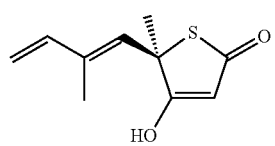 |
| TLM3 | 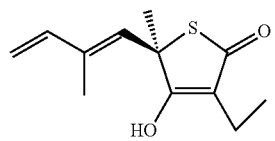 |
| TLM4 | 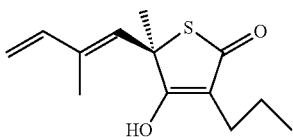 [SMILES: C=C/C(C)=C/[C@@]1(C)SC(=O)C(CCC)=C1O] |

-continued
TLM5 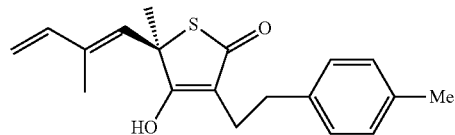 [SMILES: C=C/C(C)=C/[C@@]1(C)SC(=O)C(CCc2ccc(C)cc2)=C1O]
TLM6 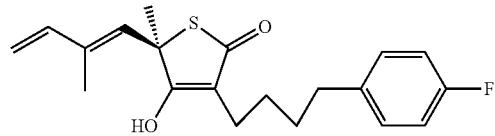 [SMILES: C=C/C(C)=C/[C@@]1(C)SC(=O)C(CCCCc2ccc(F)cc2)=C1O]
TLM7 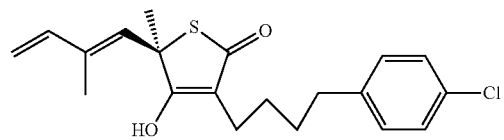 [SMILES: C=C/C(C)=C/[C@@]1(C)SC(=O)C(CCCCc2ccc(Cl)cc2)=C1O]
TLM8 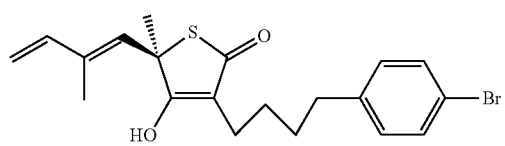 [SMILES: C=C/C(C)=C/[C@@]1(C)SC(=O)C(CCCCc2ccc(Br)cc2)=C1O]
TLM9 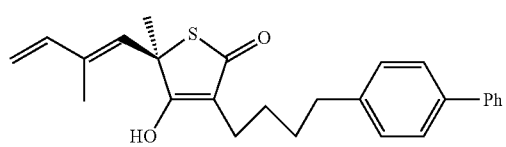
TLM10 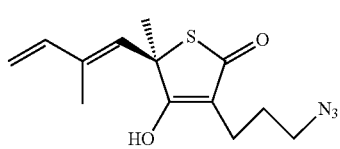 [SMILES: C=C/C(C)=C/[C@@]1(C)SC(=O)C(CCCN=[N+]=[N-])=C1O]
TLM26 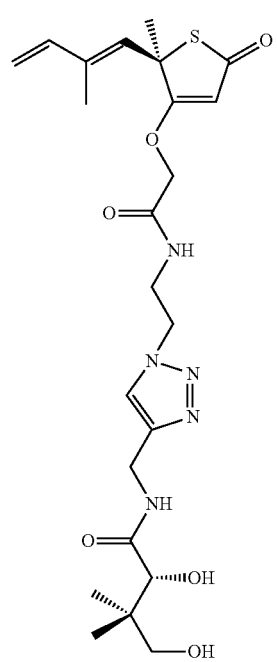

TLM31 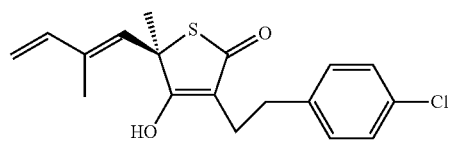 [SMILES: C=C/C(C)=C/[C@@]1(C)SC(=O)C(CCc2ccc(Cl)cc2)=C1O]
TLM32 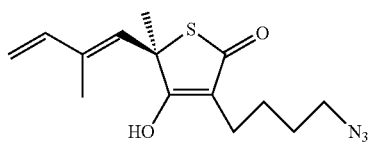 [SMILES: C=C/C(C)=C/[C@@]1(C)SC(=O)C(CCCCN=[N+]=[N-])=C1O]
TLM33 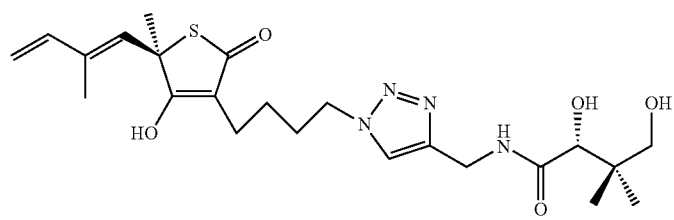
TLM34 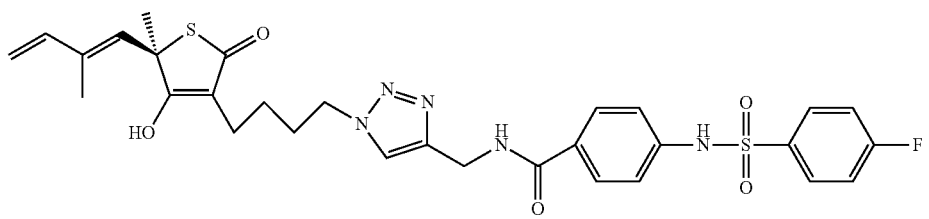 [SMILES: C=C/C(C)=C/[C@@]1(C)SC(=O)C(CCCCn2cc(CNC(=O)c3ccc(NS(=O)(=O)c4ccc(F)cc4)cc3)nn2)=C1O]
TLM35 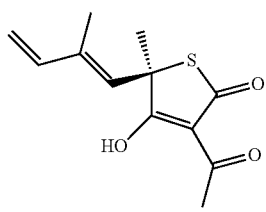 [SMILES: C=C/C(C)=C/[C@@]1(C)SC(=O)C(C(C)=O)=C1O]
TLM36 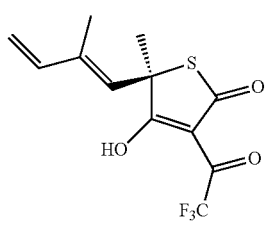 [SMILES: C=C/C(C)=C/[C@@]1(C)SC(=O)C(C(=O)C(F)(F)F)=C1O]
TLM37 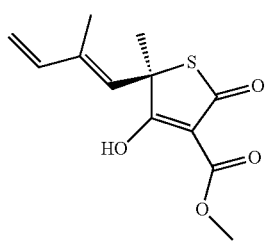 [SMILES: C=C/C(C)=C/[C@@]1(C)SC(=O)C(C(=O)OC)=C1O]

-continued
TLM38 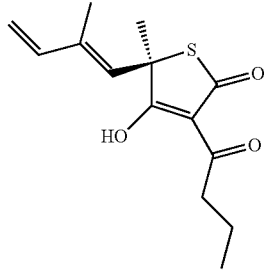 [SMILES: C=C/C(C)=C/[C@@]1(C)SC(=O)C(C(=O)CCC)=C1O]
TLM39 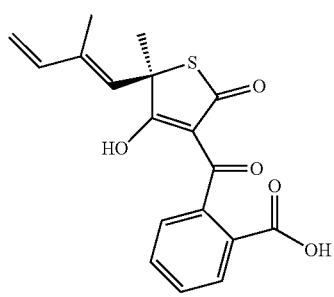 [SMILES: C=C/C(C)=C/[C@@]1(C)SC(=O)C(C(=O)c2ccccc2C(=O)O)=C1O]
TLM40 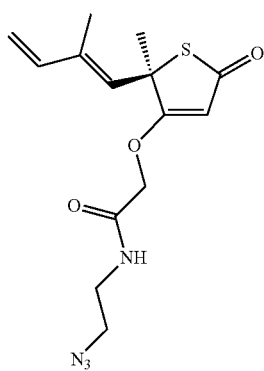 [SMILES: C=C/C(C)=C/[C@@]1(C)SC(=O)C=C1OCC(=O)NCCN=[N+]=[N-]]
TLM41 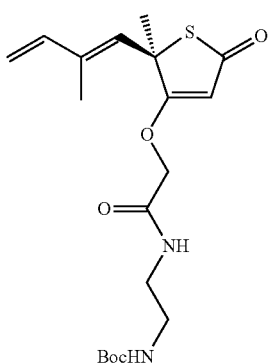 [SMILES: C=C/C(C)=C/[C@@]1(C)SC(=O)C=C1OCC(=O)NCCNC(=O)OC(C)(C)C]

TLM42
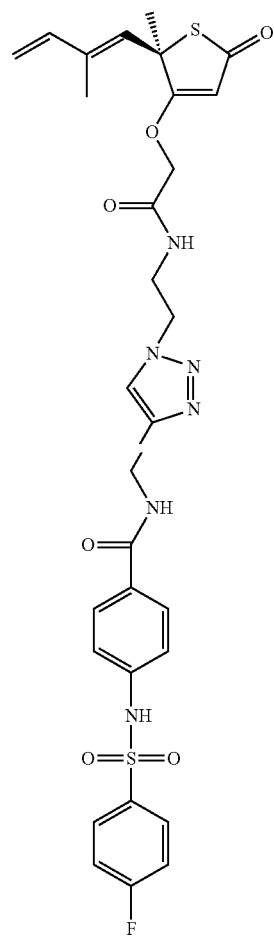 [SMILES: C=C/C(C)=C/[C@@]1(C)SC(=O)C=C1OCC(=O)NCCn1cc(CNC(=O)c2ccc(NS(=O)(=O)c3ccc(F)cc3)cc2)nn1]
TLM43
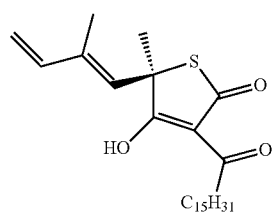
TLM44
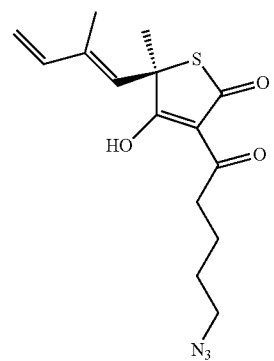 [SMILES: C=C/C(C)=C/[C@@]1(C)SC(=O)C(C(=O)CCCCN=[N+]=[N-])=C1O]

TLM45

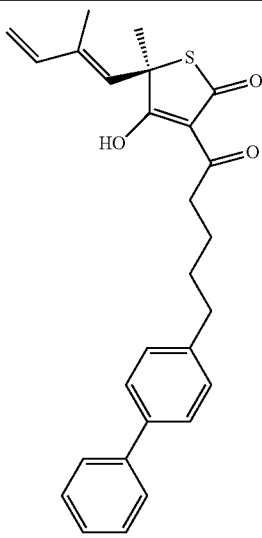

In some embodiments, a pharmaceutical composition comprising a compound of the instant invention and a pharmaceutically acceptable carrier.

Except where otherwise specified, when the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include but are not limited to phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, triazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The alkyl, aryl, and heteroaryl substituents may be substituted or unsubstituted, unless specifically defined otherwise.

The term "biphenyl" is intended to mean an aryl comprising two benzene rings linked together, and any substituted derivative thereof.

The term "pyrrole" is intended to mean a heteroaryl having a five-membered ring containing four carbon atoms and one nitrogen atom, and any substituted derivative thereof.

The term "diazole" is intended to mean a heteroaryl having a ring containing three carbon atoms and two nitrogen atoms, and any substituted derivative thereof.

The term "triazole" is intended to mean a heteraryl having a five-membered ring containing two carbon atoms and three nitrogen atoms, and any substituted derivative thereof.

The term "diol" is intended to mean any class or classes of molecules having two hydroxyl groups.

The term "piperazine" is intended to mean a heteroaryl containing two opposing nitrogen atoms, and any substituted derivative thereof.

The term "morpholine" is intended to mean a heteroaryl having a six membered ring containing four carbon atoms, and one nitrogen atom opposing one oxygen atom, and any substituted derivative thereof.

The term "piperidine" is intended to mean a heteroaryl having a six-membered ring containing five carbon atoms and one nitrogen atom, and any substituted derivative thereof.

The term "azide" is intended to mean an $N_3$ functional group.

In the compounds of the present invention, alkyl, aryl, and heteroaryl groups can be further substituted by replacing one or more hydrogen atoms be alternative non-hydrogen groups. These include, but are not limited to, halo, hydroxy, mercapto, amino, carboxy, cyano and carbamoyl.

The term "substituted" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The terms "antibacterial agent" and "antibiotic" refer to a compound, including a pharmaceutically active agent, which is useful for perturbing the growth or survival of one or more microorganisms. In preferred embodiments, microorganisms include bacteria and archaea. Antibacterial agents and antibiotics may be bacteriostatic or bactericidal, and may be classed as aminoglycosides, ansamycins, carbacephems, carbapenems, cephalosporins, glycopeptides, lincosamides, macrolides, monobactams, nitrofurans, penicillins, polypeptides, quinolones, sulfonamides, and tetracyclines, among others. Examples of antibacterial agents include, but are not limited to, TLM, amikacin, kanamycin, tobramycin, geldanamycin, hermimycin, loracarbef, ertapenem, doripenem, cefadroxil, cefalexin, cefprozil, cefdinir ceftriaxone, cefepime, teicoplanin, vancomycin, lincomycin azithromycin, dirithromycin, erythromycin, telithromycin, aztreonam furazolidone, ampicillin, mezlocillin, bacitracin, colistin, ciprofloxacin norfloxacin, temafloxacin mafenide sulfonamidochrysoidine, doxycycline, minocycline tetracycline, dapsone, capreomycin, isoniazid, rifabutin, streptomycin, arsphenamine, choramphenicol, tinidazole, and the like.

The term "pathogen" refers to an infectious microorganism that causes, or is capable of causing a disease in any organism. Examples of pathogens include, but are not limited to pathogenic species or strains of the following genuses of bacteria: *Bacillus, Bordetella, Borellia, Brucella, Burkholderia, Campylobacter, Chlamidia, Clostridium, Corynebacterium, Enterococcus, Escherichia, Francisella, Haemophilus, Helicobacter, Klebsiella, Legionella, Leptospira, Listeria, Mycobacterium, Neisseria, Pasteurella, Pseudomonas, Rickettsia, Salmonella, Serratia, Shigella, Staphylococcus, Streptococcus, Treponema, Vibrio*, and *Yersinia*.

As used herein, abbreviations are defined as follows:
Ac=acetyl
DMF=N,N-dimethylformamide
DCM=dichloromethane
THF=tetrahydrofuran
TFA=trifluoroacetic acid
THF=tetrahydrofuran
MeOH=methanol
EtOH=ethanol
DCE=1,2-dichloroethane
Ph=phenyl
Me=methyl
Et=ethyl The compounds of the instant invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compositions of this invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds of the instant invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds and compositions of the invention can be coated onto stents for temporary or permanent implantation into the cardiovascular system of a subject.

The compounds and compositions of the present invention are useful for the prevention and treatment of bacterial infections and diseases resulting from bacterial infections, such as tuberculosis.

An aspect of the invention provides a method for treating a bacterial infection in a subject suffering from a bacterial infection, comprising administering to the subject a compound of the invention.

In some embodiments, the subjected is infected with *M. tuberculosis* or a pathogenic strain of *E. coli*.

Another aspect of the invention provides a pharmaceutical composition, comprising a compound of the invention.

In some embodiments, a compound of the invention is used as an antibiotic.

In some embodiments, a compound of the invention is used for the treatment of a bacterial infection in a subject in need of treatment of a bacterial infection.

In some embodiments of the invention, a compound of the invention is used for the inhibition of bacterial cell growth.

In some embodiments, a compound of the invention is used for the prevention of a bacterial infection.

A "TLM target" as described herein refers to any polypeptide that interacts with TLM in a specific way, resulting in the inhibition of any function of that polypeptide. In preferred embodiments, TLM targets are the FASII β-ketoacyl-ACP synthase (KAS) enzymes. Furthermore, TLM targets include both KAS acyl-enzyme intermediates, as well as free KAS enzymes.

Enzymes in the microbial fatty acid biosynthesis (FASII) pathway are underexploited targets for the development of novel chemotherapeutics. Embodiments of the current invention include a series of TLM analogues, which may be potent inhibitors of the FASII β-ketoacyl-ACP synthase (KAS) enzymes. In one embodiment, the TLM analogues inhibit the KAS enzymes from *Mycobacterium tuberculosis*. In another embodiment, the TLM analogues inhibit the KAS enzymes of *Escherichia coli*. One of ordinary skill in the art will realize that the KAS inhibitors of the present application will have activity against many microorganisms, including both Gram positive and Gram negative pathogens. In some embodiments, TLM analogues of the present invention have long residence times on their drug targets based on the premise that drug-target residence time is a critical factor for in vivo activity. TLM is a slow onset inhibitor of KasA from *M. tuberculosis* and FabB from *E. coli* with residence times of 42 and 1.4 min on each enzyme, respectively.

KasA is a component of the fatty acid biosynthesis pathway in *M. tuberculosis* and catalyzes the decarboxylative Claisen condensation of malonyl-AcpM with the growing acyl chain. The active site of KasA, and other ketoacyl synthase (KAS) enzymes, is comprised of two adjacent binding sites, one that accommodates the acyl chain covalently attached to the active site cysteine (C171) and an adjacent site in which the malonyl-AcpM binds and decarboxylates during C—C bond formation (6, 23, 25).

TLM is a structural mimic of the malonyl substrate for the KAS enzymes and thus binds more tightly to the KAS acyl-enzyme than to the free enzyme. Replacement of the active site cysteine in the KAS enzymes with a glutamine results in an enzyme that mimics the acyl-enzyme intermediate (7) and that can be used in direct binding assays for assessing the affinity of compounds for the KAS acyl-enzyme for comparison with the free enzyme. Overexpressed and purified KAS enzymes from *M. tuberculosis*, *E. coli*, and additional microorganisms may be used to evaluate the affinity of TLM analogues for their targets. Initial assessments of potency may include $IC_{50}$ measurements, direct binding measurements or determinations concerning whether any of the compounds are slow onset inhibitors. The interaction of promising analogues with KAS enzymes may be explored in more detail using detailed kinetic methods and X-ray crystallography, while additional design may utilize fragment-based inhibitor assembly driven by NMR spectroscopy.

Fluorescence based direct binding studies of newly synthesized analogs may be carried out with KasA, acyl and C171Q KasA and their *E. coli* homologues. Enzymatic assays to measure the $IC_{50}$ values or the Ki (or Ki*) values of the analogs may also be performed. A KAS enzyme assay has been established, including assays for the enzymes from *M. tuberculosis* and *E. coli* (15). Additional assays for the KAS system based on the acyl carrier proteins from different organisms may also be performed.

The antibacterial activity of all compounds may be tested against pathogens. The in vivo antibacterial activity of compounds of this invention may be assessed in appropriate animal models of infection. Due to the broad spectrum antibacterial activity of TLM, it is expected that TLM analogues will be effective antibiotics against a broad array of bacteria. Therefore, the activity of all compounds may be tested for use against pathogens known to infect a variety of hosts, including but not limited to aquatic organisms (including fish cultivated in farms), birds (including poultry), and mammals (including livestock and humans).

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Transient 1D Nuclear Overhouser Effect (NOE) NMR Spectroscopy for Fragment-Based Inhibitor Discovery Studies have shown that observations of interligand NOE (ILOE) between small molecule ligands can be used as a powerful tool to aid and guide fragment based drug discovery (28-30). If two or more small molecules bind to a macromolecule in close proximity to each other, the strong negative ILOEs that develop in their bound complex geometries can be observed even in the presence of sub-stoichiometric amounts of the target provided that there is a rapid exchange between bound and free state (30). Pairs of suspected weak inhibitors can be chosen as prospects for binding to a protein either based on structural characteristics or by screening chemical libraries. Protein mediated ILOE can then assist in pharmacophore identification, and can guide the design and synthesis of bidentate ligands using these weak binding fragments as building blocks.

TLM, a natural product with broad spectrum antibacterial activity, is an inhibitor of the KAS enzymes (4, 6, 15, 16, 37), and binds more tightly to the KasA acyl-enzyme intermediate, consistent with the knowledge that TLM is a mimic of the malonyl group (15).

Although slow onset kinetics are observed when TLM binds to acyl-KasA, the inhibitor only has a Ki* value of 2 μM for the C171Q acyl-enzyme mimic (7, 38, 39), and there is thus interest in optimizing the interactions between TLM and the enzyme to improve both affinity and selectivity. Ultimately, this may be accomplished by retaining the slow onset component to the inhibition since slow onset inhibitors have long residence times on their targets (42 min for TLM), a fact that may be important for the in vivo activity of many drugs (26, 27). In order to direct the synthesis of TLM analogues, NMR spectroscopy was used to identify small molecules that bind adjacent to TLM and that can be used for fragment-based inhibitor assembly. Since TLM binds at the end of a tunnel that delivers the malonyl group, this example is focused on an analog of the pantetheine carrier (PK940).

Conflicting 1H NMR assignments have been reported for some of the TLM resonances in earlier literature (18), therefore the 1H and 13C NMR spectra for the TLM samples were reassigned to value obtained from our 1H 1D, 1H-1H COSY, 1H-13C HMQC and HMBC NMR data. These assignments agree with values presented in more recent literature (40). The methyl peaks of TLM at C6, C7, and C12 are assigned to the resonances at 1.41 ppm, 1.50 ppm and 1.44 ppm, respectively. For the PK940 ligand, non-prochiral assignments of the singlet proton peaks at 0.714 ppm and 0.75 ppm are made to the geminal methyl groups at C9' and C10' and the doublet of doublets centered near 0.708 ppm is assigned to the terminal methyl protons at C1' The overlap of the PK940 C1' methyl resonance with the upfield C9'/C10' methyl singlet hinders the analysis of the standard 1D 1H and 2D NOESY spectra.

The 1H NMR of TLM and PK940 was as follows: 1H NMR spectrum of TLM and PK940 in $D_2O$ at 700 MHz. TLM (1) 1H NMR (D2O) 6.23 (dd, 1H, H10), 5.45 (s, 1H, H8), 5.1 (d, 1H, H11, J=18 Hz), 4.9 (d, 1H, H11, J=10.4 Hz), 4.7 (H2O), 1.50 (s, 3H, H7), 1.44 (s, 3H, H12), 1.41 (s, 3H, H6). The TLM methyls at position 6, 7 and 12 are at 1.41, 1.50 and 1.44 ppm respectively. PK940 (2) 1H NMR (D2O) 3.81 (s, 1H, H6'), 3.35 (d, 1H, H8'), 3.22 (d, 1H, H8'), 3.06 (dd, 2H, H4'), 1.32 (dd, 2H, H3'), 1.15 (dd, 2H, H2'), 0.75 (s, 3H, prochiral H9'/H10'), 0.714 (s, 3H, prochiral H9'/H10'), 0.708 (dd, 3H, H1'). Stacked doublet of doublets (H1', 0.708 ppm) were resolved from geminal methyl peaks (H9' and H10', 0.714 and 0.75 ppm) examining HMQC, HMBC data and DPFGSE line shapes.

Figure 5:
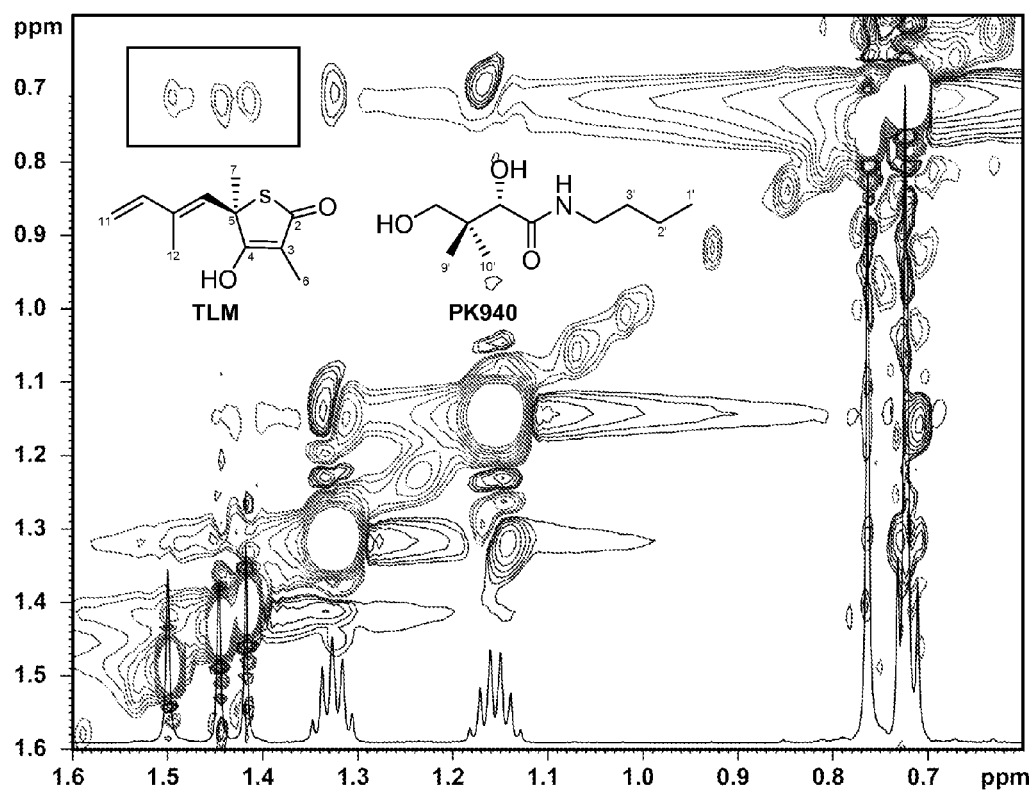
FIG. 5. 2D NOESY spectra in the presence of C171QKasA, TLM and PK940 recorded on a 700 MHz Brüker Avance instrument at a mixing time of 700 msec. Negative (red) inter-ligand NOE cross peaks can be observed between the TLM methyls at 1.41, 1.44 and 1.50 ppm and the terminal PK940 methyl doublet. Positive (Blue) intraligand NOE cross peaks can be seen between terminal PK940 methyl and C2' and C3' methylenes.

After revisiting the assignments of TLM, a 2D NOE experiment was performed (28, 30, 41). Close inspection of the 2D NOE spectra in FIG. 5 show apparent negative ILOE cross-peaks between the C6, C12, and C7 TLM methyl resonances at 1.41, 1.44 and 1.50 ppm, respectively and the PK940 methyl cluster peaks spanning 0.71-0.75 ppm. The cross peaks have chemical shifts equal to the other C2' and C3' NOE signals observed from the PK940 methylene groups at 1.15 and 1.32 ppm, respectively. Given the close proximity of the geminal C9' and C10' methyls, it is expected that they would have similar NOEs to any point on TLM. Therefore, the presence of only one associated ILOE eliminates the geminal methyls as the interacting partners with TLM.

Figure 6:
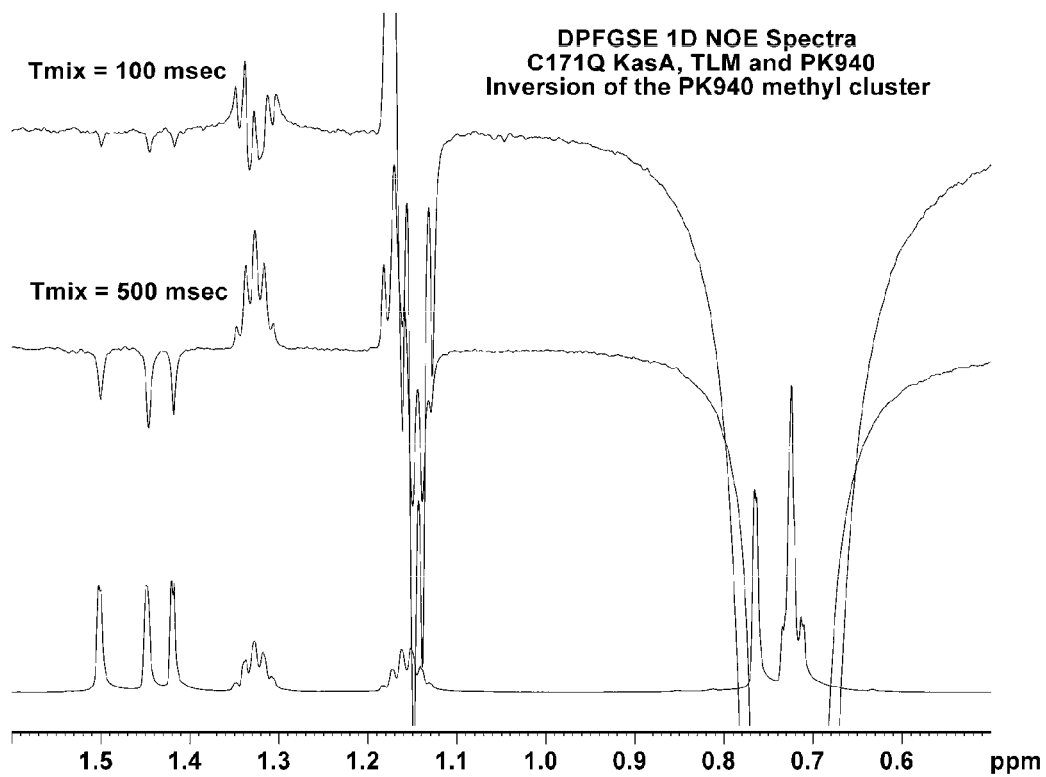
FIG. 6. Overlay of 1H NMR DPFGSE 1D NOE spectra of the ligands in the presence of C171QKasA with mixing times of 100 and 500 msec. Negative interligand NOE's can be seen with the TLM methyl resonances upon inversion of the PK940 methyl cluster at ~0.75 ppm with a 120 msec shaped Gaussian pulse. Anti-phase contributions are observed in the line shapes of the C2' and C3' methylene protons of PK940 at 1.15 ppm and 1.32 ppm due to possible strong coupling or Zero-Quantum artifact that were not removed by the DPFGSE pulse sequences that were used. (35)
Figure 8:
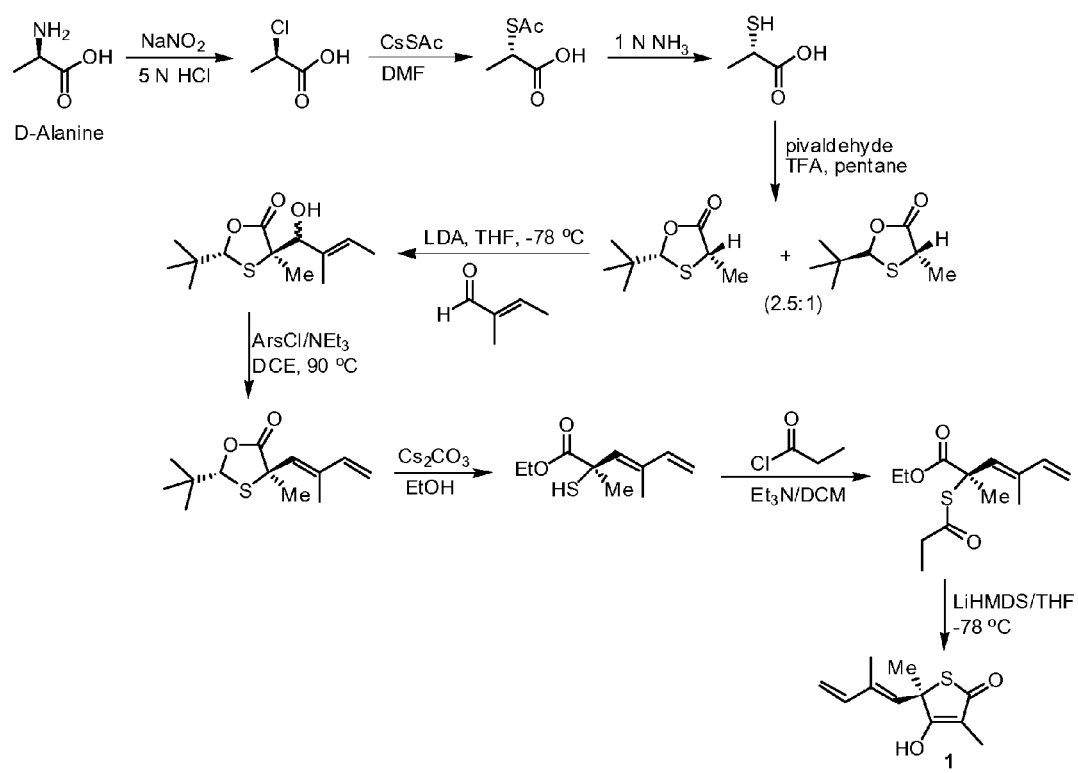
FIG. 8. Synthesis of 5R-TLM from D-alanine.

However, lack of sensitivity and the inability to detect and differentiate signal in the presence of overlapping chemical shifts and high background noise make 2D NOESY sub-optimal for ILOE detection involving small molecules (34). Interligand NOEs between TLM and the pantetheine analog (PK940) were observed at mixing times longer than 500 msec. It was possible to obtain 1D NOE data using the DPFGSE method, inverting the PK940 methyl cluster signal at ~0.75 ppm. Due to enhanced sensitivity, the 1D experiment (34, 35) allowed the detection of the ILOE signal even at very low mixing times (~100 msec) providing very clean and easily interpretable spectra. Moreover, the acquisition times were greatly reduced for the 1D experiment which also improved the quality of the data given that the enzyme was not very stable over long periods of time in the experimental conditions. The 1D NOE experiment also indicated the presence of transient inter-ligand NOEs between the three TLM methyls and the PK940 methyl cluster in the presence of the enzyme (FIG. 6). Moreover, the simultaneous selective inversion of the three TLM methyl groups allowed us to specifically assign these ILOEs to interactions between the three TLM methyl groups and the terminal C1' methyl of PK940.

NOE build up curves were obtained for the three TLM methyls over a range of mixing times (FIG. 7a). Moreover, the NOE intensities normalized with respect to the inverted peak intensity were plotted against the mixing time to obtain build ups that, to a large extent, cancel the effect of external relaxation at moderate mixing times6 (FIG. 7b). Using the distance between the TLM vinyl protons on C11 (1.85 Å) as a reference, calculated distances of 3.0 Å, 3.4 Å, 3.4 Å were obtained separating the C1' PK940 methyl and TLM C12, C6 and C7 respectively. However, the intraligand NOEs build up mainly on a short T1 regime of the unbound ligand, while the interligand NOEs build up in the bound state with the long T1 regimes of the protein. Hence, the estimated distances can, at most, be considered as qualitative constraints. However, these estimates can prove to be valuable constraints for modeling studies involving these ligands.

Subsequently, it was desirable to obtain build up curves by inverting the three TLM methyls individually and observing the interligand NOE with the terminal methyl of PK940. This turned out to be a challenging task for a number of reasons. Firstly, the chemical shifts of the three TLM methyls are very close, making individual inversion problematic. Use of a higher magnetic field (900 MHz) increased the separation of the three peaks sufficiently to provide selectivity in the absence of the enzyme. However, upon addition of enzyme, a loss of selectivity was observed, wherein inversion of all three methyls was observed upon inversion of any one, especially at higher mixing times. This observation can be explained by proposing that the dipolar coupling between KasA and TLM provides a route for cross-relaxation between the KasA methyls/methylenes and TLM methyls by the spin diffusion mechanism (21). Attempts to target the PK940 methyl cluster at ~0.71 ppm and the singlet at 0.75 ppm exclusively on a 900 MHz field, also resulted in a loss of selectivity that worsened at higher mixing times. Moreover, the expected line broadening due to modulation in the transverse relaxation time (T2) in the bound and the unbound state of the ligands could also contribute to the observed loss of selectivity.

Figure 2:
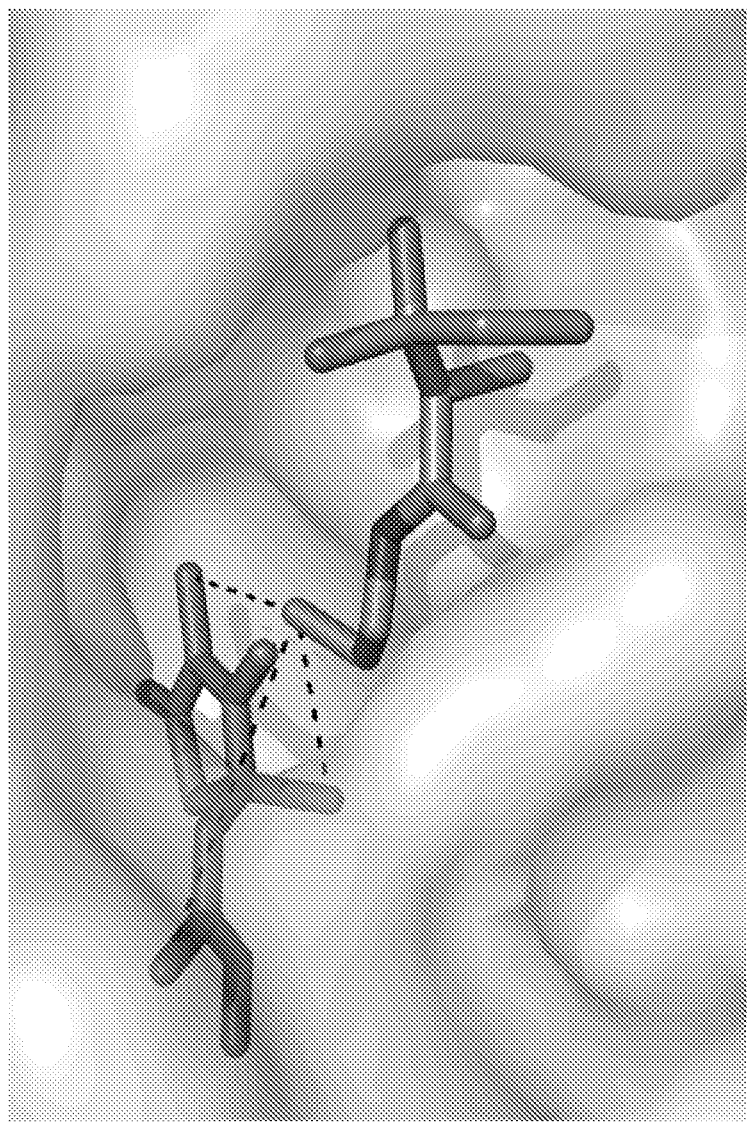
FIG. 2. Relative orientation of TLM and PK940 in the C171QKasA active site. The figure was made using Pymol (The PyMOL Molecular Graphics System, Version 1.2r3pre, Schrödinger, LLC.)

Various controls were performed to confirm that the observed signal was indeed an interligand NOE, between TLM and PK940, that develops only in the bound state. Firstly, the experiments were repeated in the absence of the enzymes as a control. No ILOE was observed between the two ligands. Secondly, the bandwidth at ~0.75 ppm was irradiated in the presence of only TLM bound to the enzyme, with the result that no signal was observed at ~1.45 ppm, where as negative ILOEs were previously observed in the presence of PK940. Subsequently, the methyl bandwidth at ~1.45 ppm was irradiated in the presence of only PK940 bound to the enzyme, and as expected no signal was observed at ~0.75 ppm. These negative controls confirmed the presence of interligand NOEs between TLM and PK940 with the terminal methyl of PK940 pointing toward the TLM methyls. Using this information PK940 was modeled into the active site of KasA using the X-ray structure of the TLM:C171QKasA complex (25). In this model PK940 occupies the putative KasA pantetheine binding pocket with the terminal methyl group of the analog oriented toward the bound TLM molecule (FIG. 2).

The interligand nuclear Overhauser effect is a powerful tool to aid fragment based drug discovery. Standard 2D NOE techniques have traditionally been used towards this end. However, long experimental times, background noise issues and lack of sensitivity limit the application of this technique especially for time sensitive samples. Here, the DPFGSE pulse sequence was used successfully to obtain NOEs between ligands bound to a protein. This technique enables cleaner NOE spectra to be obtained more rapidly over a wide range of mixing times. The NOEs and the subsequent orientations obtained from this method provide useful constraints for future modeling experiments by limiting the degrees of freedom. Also, they aid in lead optimization and guiding development of new analogs with potentially better binding affinities to the target.

Herein below, in the following Examples 2-6, novel TLM analogs targeting KasA are disclosed, the design of which is supported by the finding that elaboration of TLM at the 3 and 4 positions results in improved interaction with a target of TLM.

Experimental Procedures

Chemicals: 5-(±)-Thiolactomycin (TLM) was obtained from Sigma Aldrich Chemical Co. The 5R-TLM and the pantoylamide analog PK940 were synthesized.

Synthesis of 5R-TLM: 5R-TLM was synthesized as described in McFadden et al., 2002.

Figure 9:
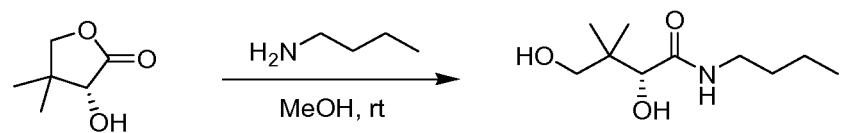
FIG. 9. Synthesis of pantoylamide PK940.

Synthesis of PK 940: PK 940 was synthesized as per published protocol (FIG. 9) (44, 45). 1H & 13C NMR spectra are provided as follows: 1H NMR of PK940. R)—N-butyl-2,4-dihydroxy-3,3-dimethylbutanamide (PK940): 1H NMR (300 MHz, CDC13) δ 0.92 (s, 3H), 0.94 (t, J=8.6 Hz, 3H), 0.98 (s, 3H), 1.36 (sextet, J=8.6 Hz, 2H), 1.49 (m, 2H), 3.15-3.36 (m, 2H), 3.47 (s, 2H), 3.71-4.31 (s, br, 2H), 4.01 (s, 1H), 6.89 (t, br, J=5.8 Hz, 1H). 13C NMR of PK940. R)—N-butyl-2,4-dihydroxy-3,3-dimethylbutanamide (PK940): 13C NMR (75.5 MHz, CDC13) δ 13.9, 20.2, 20.3, 21.4, 31.7, 39.0, 39.4, 71.4, 77.5, 173.7. MS spectra (HRMS (ESMS) calculated for C10H22NO3 [M+H+] 204.1600. found 204.1615.

Enzymes: C171QKasA was purified from *Mycobacterium smegmatis* mc2155 strain as described previously (15). Following purification the enzyme was stored in 50 mM Tris-HCl buffer pH 8.5 containing 150 mM NaCl.

Preparation of NMR samples: C171QKasA was exchanged into 50 mM sodium phosphate D2O buffer pH 8.1 containing 150 mM NaCl. 5R, S-TLM and PK940 were dissolved in phosphate buffer to give final concentrations in the experiment of 8 mM and 4 mM, respectively. For the optically active 5R-TLM, a concentration of 4 mM was used for the experiments. The concentration of enzyme in the experiments was 30 μM.

2D and 1D NOE Spectroscopy: All NMR data were acquired on standard bore 700 MHz and 900 MHz Brüker Avance NMR instruments in D2O solvents at 15° C. and processed with Brüker TOPSPIN 2.1 software.

2D NOESY spectra were collected at 700 MHz over a range of mixing times (50-900 ms) using a spectral width of 7716.05 Hz in F2 and 2048 complex data points for an acquisition time of 0.133 s with a 2 s recycle delay. 256 points were collected in the indirect F1 dimension for a 0.0166 s acquisition time. 40 scans were collected per F1 increment and F1 quadrature detection was achieved using the States-TPPI method5. Time domain data were apodized using squared sine bell functions in both dimensions and zero-filled in the indirect dimension to a final data matrix size of 1024 (F1)× 2048 (F2) after Fourier transformation.

Selective 1D DPFGSE NOE data were collected using a spectral width of 14005.6 Hz and 32768 complex data points for a 1.17 s acquisition time with a 2 s recycle delay. Selective Gaussian pulses of 120 μs were used to invert the target resonances in the PK940 methyl cluster to observe inter-ligand transfer of NOEs to the TLM methyl groups (34, 35).

Example 2

Design of Novel TLM Analogues

In order to direct the synthesis of TLM analogues, NMR spectroscopy was used to identify small molecules that bind adjacent to TLM facilitating fragment-based inhibitor assembly. Inhibitors with sub-micromolar affinity against KasA may be developed with the assistance of a fragment based approach utilizing NMR and X-Ray crystallography as discussed above in Example 1. The structure of TLM bound to several KAS enzymes (25) has been solved, and the use of inter-ligand NOE (ILOE) NMR spectroscopy (28-30) to guide fragment-based elaboration of the TLM thiolactone core is described for the first time herein as Example 1. Using protein-mediated ILOEs together with the X-ray structural studies, the orientation of a bound pantetheine fragment (PK940) close to the bound TLM molecule in the active site of C171Q KasA was determined (FIG. 2). Thus, in specific embodiments of the invention, TLM analogues have a pantetheine coupled with the TLM molecule (compound 25 in FIG. 4). The ILOE NMR studies described hereinabove show that elaboration of the TLM 3 and 4 positions as described in this invention leads to increased contacts between the ligand (the TLM analogue) and the enzyme (the TLM target), and hence higher affinity between the ligand and the enzyme. Thus the compounds of the invention have improved interaction and inhibition of a TLM target.

The synthetic schemes described in the present invention overcome two challenges. Firstly, since most published procedures have focused on 5 position analogs, an efficient scheme for modifying TLM at the 3 and 4 positions was required. Secondly, since only one enantiomer of TLM is active (R stereochemistry at the 5 position), it is necessary to ensure that the product is optically active. Most previous synthetic efforts have led to racemic TLM, with 50% of the product being in the wrong conformation to be biologically active. Consequently, in the current application, the synthesis of optically active (5R)-TLM is optimized. It is these synthetic advances that provide a unique platform to thoroughly explore chemical space around the TLM molecule and to develop analogs with higher affinity for the enzyme target. Furthermore, the TLM analogues of the present invention which are synthesized by modifying TLM at the 3 and/or 4 positions, have improved affinity for the enzyme target(s) of TLM.

Example 3

Synthesis of 3 Position TLM Analogues

Figure 3:
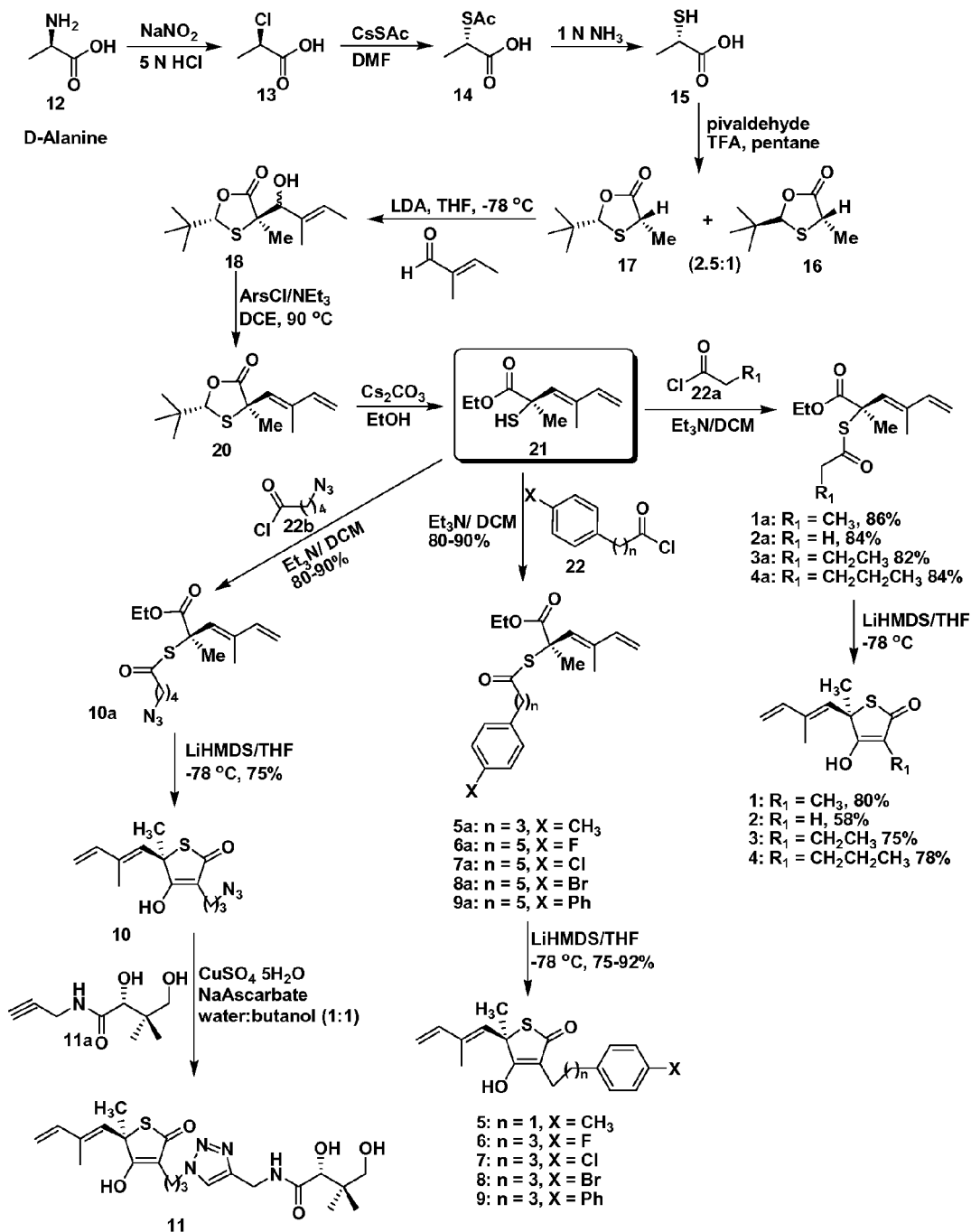
FIG. 3. Synthesis of TLM analogues at the 3 position.

The following procedures relate to the synthesis scheme shown in FIG. 3:

Procedure A.

Cesium carbonate (1.6 mmol) was added directly to a solution of 20 (1.6 mmol) in EtOH (6.0 mL). After 20 min this mixture was poured into NH4Cl (sat.)/1 N HCl (15 mL, 3:1) and extracted with Et2O (3×20 mL) and then water (3×20 mL). The combined organics were dried (MgSO4), filtered, evaporated, and redissolved in CH2Cl2 (15 mL). To this pre-cooled solution at 0° C. were added NEt3 (2.0 mmol) and acid chloride (22, 22a, 22b) (1.6 mmol). After 40 min NH4Cl (sat) (20 mL) was added, and this mixture was extracted with CH2Cl2 (3×15 mL). The combined organics were dried (MgSO4), filtered, and evaporated. Flash chromatography (5% EtOAc/hex) gave pure 1a-10a; yield (80-90%).

Procedure B.

To 1a-10a (1.09 mmol) in THF (16.4 mL) at −78° C. was added LiHMDS (1.8 mmol, 1.0 M in THF), and the solution was allowed to slowly warm to −5° C. The solution was then poured into 1 N HCl (25 mL) and extracted with EtOAc (3×15 mL). The combined organics were dried (MgSO4), filtered, and evaporated. This crude mixture was taken up in NaHCO3

(sat, 15 mL) and stir for 15 min and extracted with Et$_2$O (3×10 mL). The aqueous layer was then acidified to pH 3 (pH paper) with 1 N HCl and extracted with Et$_2$O (3×10 mL) and EtOAc (2×10 mL). The combined organics were dried (MgSO$_4$), filtered, and evaporated to provide pure 1-10; yield (58-92%).

Compounds 1 and 2 in FIG. 3 may be synthesized as reported in McFadden et al., 2002, the content of which is hereby incorporated by reference.

Example 4

Synthesis of 3 and 4 Position Analogues and Analysis

Figure 4:
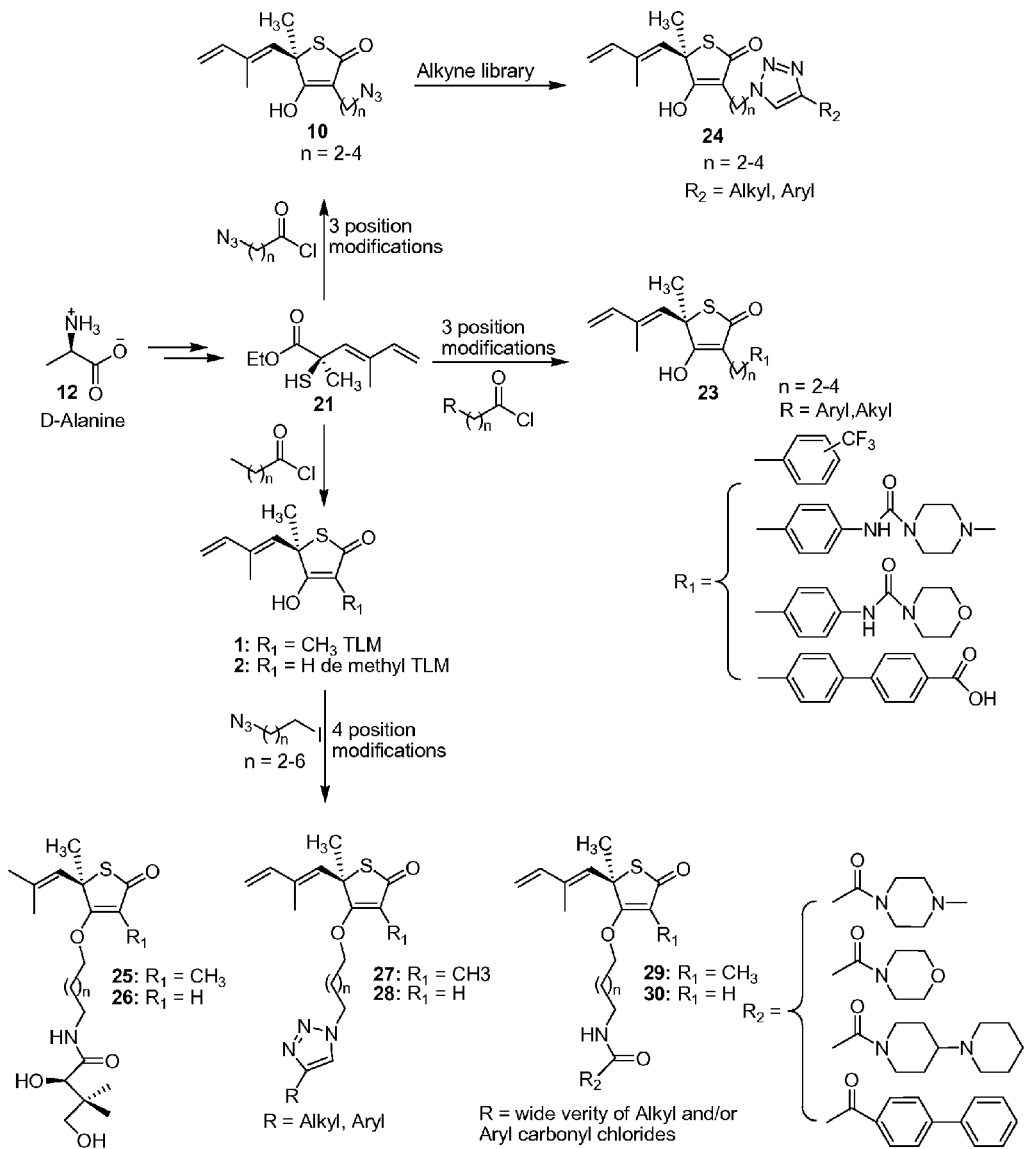
FIG. 4. TLM analogues at the 3 and 4 positions.

Synthesis of 3 and 4 position TLM analogues is shown in FIGS. 3 and 4 and initially follows the asymmetric synthesis of (5R) TLM from D-alanine described by Townsend and coworkers (31). Methods developed in the present application enabled the synthesis of (5R)-TLM and some 3 position TLM analogues (FIG. 3, 2-11). An important aspect of the method in the current invention involves the incorporation of appropriate acid chlorides on intermediate 21, and followed by thio-Dieckman reaction to provide wide variety of 3-substituted (5R)-TLM analogues (FIG. 3).

As mentioned hereinabove, compound 21 (FIG. 4) has been synthesized from D-alanine (Compound 12). Compound 21 can be coupled with 5-azidovaleryl chloride to generate compound 10 (31) and a variety of chloroacetyl derivatives to obtain 3-substituted TLM analogs 23 (FIG. 4). Subsequently, 24 can be synthesized from 10 using 'Click' Chemistry. Also, substituting an azido (N$_3$) group on the TLM Thiazole ring at the 3$^{rd}$ or 4$^{th}$ position, allows many different functionalities to be attached to the molecule via reactions such as those of Click Chemistry. Click chemistry is a modular approach to chemical synthesis that uses a set of powerful, highly reliable, and selective reactions for the rapid synthesis of useful new compounds. Click chemistry, a 2,3 cycloaddition between an terminal alkyne and an azide catalyzed by a copper catalyst, is thoroughly reviewed and described in: H. C. Kolb, K. B. Sharpless. The growing impact of click chemistry on drug discovery. Drug Discovery Today 2003, 8, 1128-1137; b) H. C. Kolb, M. G. Finn, K. B. Sharpless. Click chemistry: diverse chemical function from a few good reactions. Angew. Chem. Int. Ed. 2001, 40, 2004-2021, the contents of which are hereby incorporated by reference.

Alkylation of TLM at the 4 position leads to a mixture of alkylated products at the 2, 3 and 4 positions (32), potentially resulting in the generation of undesired products during the synthesis of 4 position analogues (compounds 25, 27, 29) (FIG. 4). However, it is possible to make 4 position analogues varying the base and reaction conditions to overcome this challenge (33). Compounds (compounds 25, 27, 29) can be generated from 1 with varied linker lengths following reduction of the terminal azide and coupling of the corresponding amine chloroacetyl derivatives (compound 27). Reduction of this azide followed by coupling with R-(−)-2-hydroxy-3,3-dimethyl-γ-butyrolactonepentolactone yields compound 25. Alternatively, the terminal azide can be used to generate compound 26 using Click Chemistry as described hereinabove. It is also possible to make 4 position analogues of compound 2 (3-demethyl TLM) using the same reaction sequence (compounds 26, 28, 30) (FIG. 4).

Those having ordinary skill in the art of organic synthesis will appreciate that modifications to the general procedures shown in the synthesis schemes of this application can be made to yield structurally diverse compounds. For example, where aryl rings are present, all positional isomers are contemplated and may be synthesized using standard aromatic substitution chemistry. The number and types of substituents may also vary around the aryl rings. Furthermore, where alkyl groups are present, the chain length may be modified using methods well known to those of ordinary skill in the art. Where ester formation is contemplated, lactones may be used wherein the lactone ring is opened by reaction with a nucleophile, such as an ether-containing moiety described hereinabove. Suitable organic transformations are described in March's Advanced Organic Chemistry: Reactions, Mechanisms, and Structure (Wiley-Interscience; 6$^{th}$ edition, 2007), the content of which is hereby incorporated by reference.

Example 5

Non-Limiting Examples of Specific Compound Synthesis

Compounds were prepared using Procedure A or B as indicated below. Analysis was performed on the TLM analogues below which were produced by the indicated Procedures from Example 1, and results of the analysis are provided:

5R-(+)-Thiolactomycin (1)

Procedure B

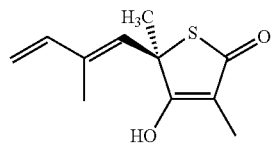

$[\alpha]_D^z$=+173.0 (c 1.2, MeOH). Mp 119-121° C.; [(lit.$^1$ $[\alpha]_D^{23}$=+174 (c 0.6, MeOH), Mp 119-121° C.)]; [(lit.$^8$ $[\alpha]_D^{23}$=+176 (c 1.0, MeOH), Mp 120° C.]. $^1$H NMR (500 MHz, CDCl$_3$ and 5% CD$_3$OD): δ 1.64, 1.65 (2s, 6H), 1.73 (s, 3H), 1.91 (s, 3H), 4.96. (d, J=11.0 Hz, 1H), 5.15 (d, J=17.0 Hz, 1H), 5.53 (s, 1H), 6.26 (dd, J=17.0, 11.0 Hz, 1H). $^{13}$C NMR (125 MHz, CDCl$_3$ and 5% CD$_3$OD) δ 7.2, 11.6, 29.3, 55.1, 109.3, 113.2, 130.0, 139.1, 140.7, 180.6, 196.5. MS (EI$^-$): 209.1 (M−1).

Synthesis of Compound 2a

Procedure A

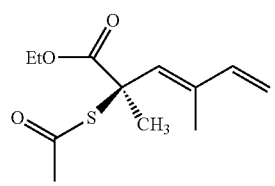 [SMILES: C=C/C(C)=C/[C@@](C)(SC(C)=O)C(=O)OCC]

$[\alpha]_D^{23}$=+17 (c 1.0 CH$_2$Cl$_2$). $^1$H NMR (600 MHz, CDCl$_3$): δ 1.25, (t, J=7.2 Hz, 3H), 1.84, 1.87 (2s, 6H), 1.21 (s, 3H), 4.20. (q, J=7.2 Hz, 2H), 5.03 (d, J=9.0 Hz, 1H), 5.20 (d, J=14.5 Hz, 1H), 5.73 (s, 1H), 6.30 (dd, J=14.5, 9.0 Hz, 1H).

$^{13}$C NMR (125 MHz, CDCl₃) δ 12.7, 13.8, 25.8, 29.9, 55.2, 61.8, 113.1, 131.1, 138.1, 141.0, 171.8, 194.3. MS (EI•): 243.1 (M+1), 201.1 (M−44)

5R-(+)-3-Demethylthiolactomycin (2)

Procedure B

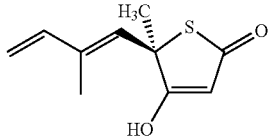

$[\alpha]_D^{23}$=+44 (c 1.0 MeOH). 1H NMR (500 MHz, CD₂OD): δ 1.79 (s, 3H), 1.83 (s, 3H), 5.06 (d, J=10.5 Hz, 1H), 5.27 (d, J=17.7 Hz, 1H), 5.66 (s, 1H), 6.36 (dd, J=17.5, 10.5 Hz). $^{13}$C NMR (100 MHz, CD₂OD): δ 12.4, 30.3, 58.8, 113.7, 131.4, 140.5, 142.1, 190.1, 197.2. MS (EI⁺): 197.1 (M+1).

Synthesis of Compound 3a

Procedure A

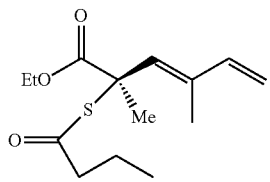 [SMILES: C=C/C(C)=C/[C@@](C)(SC(=O)CCC)C(=O)OCC]

$[\alpha]_D^{23}$=+32 (c 1.0 CH₂Cl₂). ¹H NMR (400 MHz, CDCl₃): δ 0.88, (t, J=7.2 Hz, 3H), 1.21 (t, J=7.2 Hz, 3H), 1.58-1.64 (m, 2H), 1.82, 1.84 (2s, 6H), 2.40 (t, J=7.2 Hz, 3H), 4.13-4.18 (m, 2H), 5.00 (d, J=10.8 Hz, 1H), 5.20 (d, J=17.2 Hz, 1H), 5.72 (s, 1H), 6.30 (dd, J=17.2, 10.8 Hz, 1H). $^{13}$C NMR (100 MHz, CDCl₃) δ 12.7, 13.8, 18.9, 25.9, 45.1, 55.0, 61.8, 113.0, 131.2, 131.3, 138.1, 141.0, 172.0, 198.0. MS (EI•): 285.1 (M+1).

5R-(+)-3-Ethylthiolactomycin (3)

Procedure B

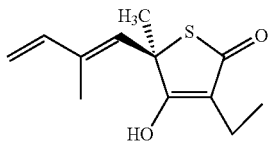

$[\alpha]_D^{23}$=+98.0 (c 1, MeOH). ¹H NMR (500 MHz, CDCl₃ and 5% CD₂OD): δ 1.97 (t, J=7.2 Hz, 3H), 1.68, 1.77 (2s, 6H), 2.24 (q, J=7.2 Hz, 2H), 4.98. (d, J=10.5 Hz, 1H), 5.18 (d, J=17.0 Hz, 1H), 5.53 (s, 1H), 6.26 (dd, J=17.0, 10.5 Hz, 1H).

$^{13}$C NMR (125 MHz, CDCl₃ and 5% CD₂OD) δ 11.6, 12.2, 29.6, 55.0, 113.5, 115.3, 130.0, 139.4, 140.7, 180.6, 196.3. MS (EI⁻): 223.1 (M−1).

Synthesis of Compound 4a

Procedure A

¹H NMR (400 MHz, CDCl₃): δ 0.85, (t, J=7.2 Hz, 3H), 1.22 (t, J=7.2 Hz, 3H), 1.26-1.30 (m, 2H) 1.55-1.59 (m, 2H), 1.82, 1.84 (2s, 6H), 2.43 (t, J=7.2 Hz, 3H), 4.14-4.19 (m, 2H), 5.00 (d, J=10.8 Hz, 1H), 5.20 (d, J=17.2 Hz, 1H), 5.72 (s, 1H), 6.30 (dd, J=17.2, 10.8 Hz, 1H). $^{13}$C NMR (100 MHz, CDCl₃) δ 12.8, 13.5, 13.8, 21.8, 25.9, 43.0, 55.0, 61.8, 113.0, 131.3, 131.5, 138.1, 141.2, 172.0, 198.2. MS (EI•): 271.2 (M+1).

5R-(+)-3-Propylthiolactomycin (4)

Procedure B $[\alpha]_D^{23}$=+61.0 (c 1, MeOH). ¹H NMR (500 MHz, CDCl₃ and 5% CD₃OD): δ 1.89 (t, J=7.2 Hz, 3H), 2.26-2.20 (m, 2H), 1.73, 1.85 (2s, 6H), 2.23 (q, J=7.2 Hz, 2H), 5.02. (d, J=10.5 Hz, 1H), 5.22 (d, J=17.0 Hz, 1H), 5.58 (s, 1H), 6.27 (dd, J=17.0, 10.5 Hz, 1H). $^{13}$C NMR (125 MHz, CDCl₃ and 5% CD₃OD) δ 12.0, 13.8, 21.1, 24.6, 29.8, 55.4, 113.6, 114.5, 129.3, 139.9, 140.7, 181.2, 197.5. MS (EI⁻): 237.1 (M−1).

Synthesis Compound 5a

Procedure A $[\alpha]_D^{23}$=−212 (c 1.0 CH₂Cl₂). ¹H NMR (500 MHz, CDCl₃): δ 1.28, (t, J=7.5 Hz, 3H), 1.88, 1.90 (2s, 6H), 1.20-1.93 (m, 2H), 1.33 (s, 3H), 2.25 (t, J=7.5 Hz, 2H), 2.61 (t, J=7.5 Hz, 2H), 4.23. (q, J=7.2 Hz, 2H), 5.07 (d, J=10.5 Hz, 1H), 5.24 (d, J=17.5 Hz, 1H), 5.79 (s, 1H), 6.35 (dd, J=17.5, 10.5 Hz, 1H), 7.06-7.19 (m, 4H). $^{13}$C NMR (125 MHz, CDCl$_3$) δ 13.0, 14.0, 20.1, 26.0, 27.1, 34.3, 42.6, 55.2, 113.2, 128.3, 129.0, 131.4, 135.4, 138.0, 138.2, 141.0, 172.1, 198.1. MS (EI•): 361.1 (M+1).

Synthesis of Compound 5

Procedure B

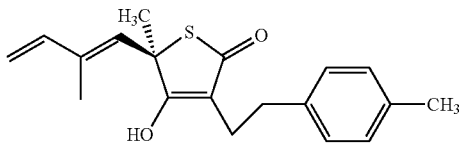 [SMILES: C=C/C(C)=C/[C@@]1(C)SC(=O)C(CCc2ccc(C)cc2)=C1O]

$[α]_D^{23}$=+161 (c 1.0 CH$_2$Cl$_2$). $^1$H NMR (500 MHz, CDCl$_3$): δ 1.70, 1.74 (2s, 6H), 2.31 (s, 3H), 2.47-2.55 (m, 1H), 2.60-2.54 (m, 1H), 2.68-2.78 (m, 2H), 5.05 (d, J=10.5 Hz, 1H), 5.24 (d, J=17.5 Hz, 1H), 5.50 (s, 1H), 6.30 (dd, J=17.5, 10.5 Hz, 1H), 7.03-7.12 (m, 4H). $^{13}$C NMR (125 MHz, CDCl$_3$) δ 12.1, 21.0, 25.2, 29.7, 33.3, 55.0, 113.8, 113.9, 128.3, 129.14, 129.16, 129.3, 135.8, 138.4, 140.1, 140.6, 179.7, 195.4. MS (EI•): 315.1 (M+1).

Synthesis of Compound 6a

Procedure A

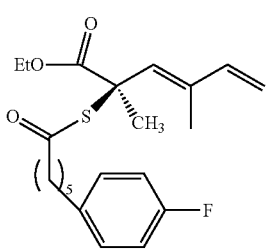

$[α]_D^{23}$=+965 (c 1.0 CH$_2$Cl$_2$). $^1$H NMR (500 MHz, CDCl$_3$): δ 1.24, (t, J=7.5 Hz, 3H), 1.26-1.34 (m, 2H), 1.35-1.67 (2m, 4H), 1.85, 1.87 (2s, 6H), 2.42-2.55 (m, 2H), 2.56-2.59 (m, 2H), 4.20. (q, J=7.2 Hz, 2H), 5.03 (d, J=9.0 Hz, 1H), 5.20 (d, J=14.5 Hz, 1H), 5.76 (s, 1H), 6.32 (dd, J=14.5, 9.0 Hz, 1H), 6.93-6.95 (m, 2H), 7.08-7.10 (m, 2H). $^{13}$C NMR (125 MHz, CDCl$_3$) δ 12.9, 13.9, 25.7, 25.9, 28.6, 30.9, 34.7, 43.1, 55.1, 113.1, 114.8, 114.9, 129.56, 131.3, 137.8, 138.1, 141.2, 160.1, 162.0, 172.0, 198.1. MS (EI•): 393.1 (M+1), 410.2 (M+NH$_4$).

Synthesis of Compound 6

Procedure B

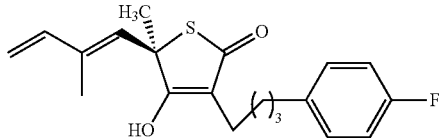

$[α]_D^{23}$=+63 (c 1.0 CH$_2$Cl$_2$). $^1$H NMR (300 MHz, CDCl$_3$) δ 1.50-1.61 (2m, 4H), 1.70 (s, 3H), 1.83 (s, 3H), 2.26 (t, J=7.2 Hz, 2H), 2.56 (t, J=7.2 Hz, 2H), 5.06 (d, J=10.5 Hz, 1H), 5.24 (d, J=17.5 Hz, 1H), 6.27 (dd, J=17.5, 10.5 Hz, 1H), 6.89-6.95 (m, 2H), 7.05-7.10 (m, 2H). $^{13}$C NMR (125 MHz, CDCl$_3$) δ 12.0, 22.3, 27.3, 29.7, 31.2, 34.7, 55.6, 114.7, 114.9, 129.5, 129.6, 138.0, 140.0, 140.6, 159.9, 162.3, 181.3, 197.7. $^{19}$F NMR (400 MHz, CDCl$_3$) 6-122.32 (m). MS (EI•): 347.1 (M+1).

Synthesis of Compound 7a

Procedure A

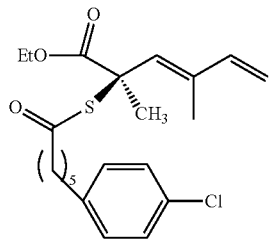

$[α]_D^{23}$=−10 (c 1.0 MeOH). $^1$H NMR (500 MHz, CDCl$_3$): δ 1.27, (t, J=7.5 Hz, 3H), 1.33-1.37 (m, 2H), 1.61-1.68 (2m, 4H), 1.87, 1.89 (2s, 6H), 2.49 (t, J=7.5 Hz, 2H), 2.56-2.60 (m, 2H), 4.20. (q, J=7.5 Hz, 2H), 5.06 (d, J=10.5 Hz, 1H), 5.23 (d, J=17.5 Hz, 1H), 5.78 (s, 1H), 6.34 (dd, J=17.5, 10.5 Hz, 1H), 7.09-7.10 (m, 2H), 7.24-7.28 (m, 2H). $^{13}$C NMR (125 MHz, CDCl$_3$) δ 12.9, 13.9, 25.2, 25.9, 28.1, 30.7, 34.8, 43.1, 55.1, 113.1, 128.2, 128.3, 129.5, 129.6, 131.2, 131.3, 138.1, 141.6, 141.2, 172.0, 198.1. MS (EI•): 409.1 (M+1), 426.2 (M+NH$_4$).

Synthesis of Compound 7

Procedure B

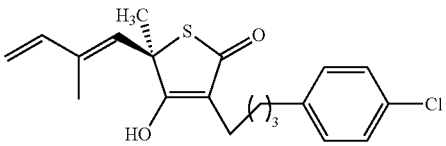

$[\alpha]_D^{23}=+48$ (c 1.0 MeOH). $^1$H NMR (500 MHz, CDCl$_3$) δ 1.50-1.62 (2m, 4H), 1.73 (s, 3H), 1.85 (s, 3H), 2.28 (t, J=7.2 Hz, 2H), 2.56 (t, J=7.2 Hz, 2H), 5.06 (d, J=10.5 Hz, 1H), 5.26 (d, J=17.5 Hz, 1H), 6.28 (dd, J=17.5, 10.5 Hz, 1H), 7.07-7.09 (m, 2H), 7.22-7.25 (m, 2H). $^{13}$C NMR (125 MHz, CDCl$_3$) δ 12.0, 22.4, 27.2, 30.2, 31.0, 34.9, 55.9, 114.2, 114.8, 128.3-129.6 (m), 131.3, 140.0, 140.4, 140.7, 179.8, 198.2. MS (EI•): 363.1 (M+1).

Synthesis of Compound 8a

Procedure A

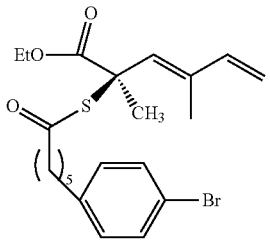

$[\alpha]_D^{23}=-70$ (c 1.0 MeOH). $^1$H NMR (500 MHz, CDCl$_3$): δ 1.27, (t, J=7.5 Hz, 3H), 1.30-1.36 (m, 2H), 1.59-1.68 (2m, 4H), 1.87, 1.89 (2s, 6H), 2.49 (t, J=7.5 Hz, 2H), 2.52-2.60 (m, 2H), 4.20. (q, J=7.5 Hz, 2H), 5.06 (d, J=10.5 Hz, 1H), 5.24 (d, J=17.5 Hz, 1H), 5.78 (s, 1H), 6.34 (dd, J=17.5, 10.5 Hz, 1H), 7.04-7.06 (m, 2H), 7.39-7.41 (m, 2H). $^{13}$C NMR (125 MHz, CDCl$_3$) δ 12.9, 13.9, 25.2, 25.9, 28.2, 30.7, 35.0, 43.2, 55.2, 113.2, 119.3, 130.0-131.4 (m), 138.2, 141.6, 172.0, 198.2. MS (EI•): 453.1 and 455.1 (M+1), 470.1 and 472.1 (M+NH$_4$).

Synthesis of Compound 8

Procedure B

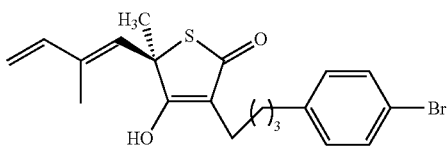

$[\alpha]_D^{23}=+57$ (c 1.0 CH$_2$Cl$_2$). $^1$H NMR (500 MHz, CDCl$_3$) δ 1.50-1.64 (2m, 4H), 1.73 (s, 3H), 1.85 (s, 3H), 2.28 (t, J=7.2 Hz, 2H), 2.56 (t, J=7.2 Hz, 2H), 5.09 (d, J=10.5 Hz, 1H), 5.26 (d, J=17.5 Hz, 1H), 6.29 (dd, J=17.5, 10.5 Hz, 1H), 7.02-7.04 (m, 2H), 7.37-7.39 (m, 2H). $^{13}$C NMR (125 MHz, CDCl$_3$) δ 12.0, 21.0, 27.2, 30.2, 31.0, 34.9, 55.0, 114.1, 114.7, 119.3, 128.8-130.1 (m), 131.3, 140.4, 140.6, 141.4, 179.5, 195.8. MS (EI•): 407.0 (M+1).

Synthesis of Compound 9a

Procedure A

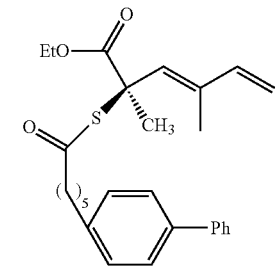

$[\alpha]_D^{23}=-158$ (c 1.0 CH$_2$Cl$_2$). $^1$H NMR (500 MHz, CDCl$_3$): δ 1.27, (t, J=7.5 Hz, 3H), 1.36-1.48 (m, 2H), 1.59-1.72 (2m, 4H), 1.89, 1.91 (2s, 6H), 2.52 (t, J=7.5 Hz, 2H), 2.65-2.69 (m, 2H), 4.24. (q, J=7.5 Hz, 2H), 5.07 (d, J=10.5 Hz, 1H), 5.25 (d, J=17.5 Hz, 1H), 5.80 (s, 1H), 6.35 (dd, J=17.5, 10.5 Hz, 1H), 7.25-7.61 (m, 9H). $^{13}$C NMR (125 MHz, CDCl$_3$) δ 12.9, 13.9, 25.3, 25.9, 28.4, 30.9, 35.2, 43.2, 55.2, 113.2, 126.9-128.7 (m), 131.4, 138.2, 138.6, 141.2, 141.4, 172.1, 198.2. MS (EI•): 451.2 (M+1), 468.2 (M+NH$_4$).

Synthesis of Compound 9

Procedure B

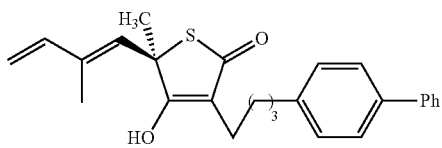

$[\alpha]_D^{23}=-91$ (c 1.0 CH$_2$Cl$_2$). $^1$H NMR (500 MHz, CDCl$_3$) δ 1.50-1.69 (2m, 4H), 1.75 (s, 3H), 1.86 (s, 3H), 2.32 (t, J=7.2 Hz, 2H), 2.67 (t, J=7.2 Hz, 2H), 5.08 (d, J=10.5 Hz, 1H), 5.26 (d, J=17.5 Hz, 1H), 6.30 (dd, J=17.5, 10.5 Hz, 1H), 7.23-7.59 (m, 9H). $^{13}$C NMR (125 MHz, CDCl$_3$) δ 12.0, 22.5, 27.4, 30.2, 31.1, 35.2, 55.0, 114.1, 114.8, 126.9-128.8 (m), 138.6, 140.5, 140.6, 141.0, 141.6, 179.4, 195.9. MS (EI•): 405.1 (M+1).

Synthesis of Compound 10a

Procedure A

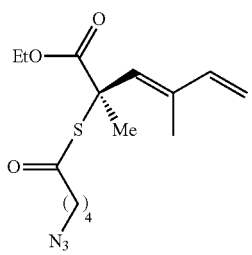

$[\alpha]_D^{23}$=−3.6 (c 1.0 CH$_2$Cl$_2$). $^1$H NMR (500 MHz, CDCl$_3$) δ 1.22 (t, J=7.2 Hz, 3H), 1.55-1.58 (m, 2H), 1.67-1.70 (m, 2H) 1.82, 1.84 (2s, 6H), 2.46-2.49 (m, 2H), 3.23 (t, J=6.5 Hz, 2H), 4.14-4.19 (m, 2H), 5.00 (d, J=11.0 Hz, 1H), 5.20 (d, J=17.5 Hz, 1H), 5.71 (s, 1H), 6.30 (dd, J=17.5, 10.8 Hz, 1H). $^{13}$C NMR (125 MHz, CDCl$_3$) δ 12.84, 12.85, 13.8, 22.5, 25.9 27.8, 42.4, 50.8, 55.2, 61.9, 113.2, 131.13, 131.16, 138.2, 141.0, 172.0, 197.5. MS (EI•): 326.0 (M+1).

Synthesis of Compound 10

Procedure B

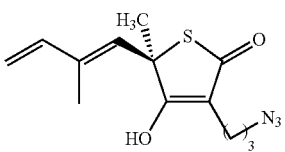

$[\alpha]_D^{23}$=+13.6 (c 1, MeOH). $^1$H NMR (500 MHz, CD$_2$OD): δ 1.21 (t, J=7.5 Hz, 3H), 1.71, 1.78 (2s, 6H), 2.26 (m, 2H), 3.26 (m, 2H), 5.02. (d, J=10.0 Hz, 1H), 5.20 (d, J=17.0 Hz, 1H), 5.54 (s, 1H), 6.27 (dd, J=17.0, 10.0 Hz, 1H). $^{13}$C NMR (125 MHz, MeOH-d4) δ 11.2, 19.4, 26.6, 29.2, 50.6, 54.7, 112.1, 113.0, 114.5, 129.3, 139.2, 140.3, 181.6, 195.9. MS (EI−): 278.0 (M−1).

Synthesis of Compound 11

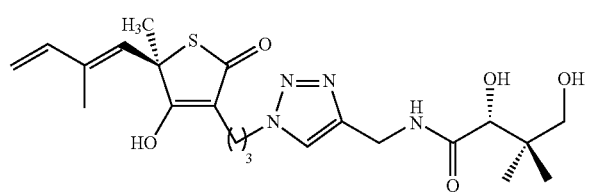

To a stirred solution of compound 10 (1.0 mmol) and Alkyne (11a) (1.0 mmol) in n-Butanol/water (1:1, 3 ml) at rt, were added CuSO$_4$.5H$_2$O (1.0 mmol) and sodium ascorbate 1.0 mmol). The reaction mixture was stirred at rt for 1-2 h then filtered and concentrated. Crude compound was purified with flash chromatography or HPLC to get corresponding click product. MS (EI−): 463.0 (M−1).

Example 6

TLM Analogue Interaction with KasA

Fluorescence spectroscopy was used to determine the K$_d$ values for the interaction of TLM analogues 1-10 with wild-type apo-KasA and the C171Q KasA acyl-enzyme mimic (15) (Table 1). The compounds of the invention have improved interaction with the targets of TLM. The TLM analogues tested bind significantly more tightly to apo-KasA compared to TLM (K$_d$~230 μM). For example, the p-phenyl derivative (FIG. 3, compound 9) has a K$_d$ value of 11 μM for apo-KasA. However, all the analogues had a weaker K$_i$* to C171Q enzyme as compared to TLM.

Without wishing to be bound by any scientific theory, it is possible that the modifications of TLM at the 3 and/or 4 positions, while increasing their interaction with apo-KasA as compared to TLM, may introduce features that interfere with a structural aspect of the KasA acyl-enzyme interaction when compared to the TLM KasA acyl-enzyme. However, each compound of the invention will have an improved interaction with apo-KasA compared to TLM. While, TLM analogues of the invention may bind less tightly (K$_i$) to the C171Q KasA than TLM, the kinetics of slow onset binding may be improved, and hence the overall binding constant, k$_{off}$ and K$_i$*, of the compounds of the invention against the acyl KasA mimic.

TABLE 1

K$_d$ values for the interaction of the TLM analogues with KasA and the C171Q KasA acyl-enzyme mimic

| Compound | | K$_d$ (μM) apo-KasA | C171QKasA K$_i$(μM) | K$_i$*(μM) |
|---|---|---|---|---|
| TLM | 1 | 229 ± 9 | 126 ± 16 | Slow, 2.2 ± 1.6 |
| demethyl TLM | 2 | 147 ± 2 | 47 ± 1 | Rapid |
| 3-Ethyl TLM | 3 | 330 ± 4 | 357 ± 35 | Slow, 7.1 ± 1 |
| 3-Propyl TLM | 4 | 255.5 ± 3 | 305 ± 8 | Slow, 16 ± 2 |
| p-methyl TLM | 5 | 150 ± 3 | 93 ± 1 | Rapid |
| p-fluoro TLM | 6 | 71 ± 1 | 69 ± 2 | Rapid |
| p-chloro TLM | 7 | 68 ± 1 | 77 ± 1 | Rapid |
| p-bromo TLM | 8 | 71 ± 1 | 82 ± 2 | Rapid |
| p-phenyl TLM | 9 | 11 ± 1 | 14 ± 1 | Rapid |
| 3-Azido TLM | 10 | 233.3 ± 7 | Slow Onset | Slow, ND |

Binding of TLM and analogs was quantified (Table 2) using the intrinsic tryptophan fluorescence of wt and C171QKasA using a Quanta Master fluorimeter (Photon Technology International). The fluorophore was excited at 280 nm and the emission was monitored at 337 nm, with an excitation slit width of 4.0 nm and an emission slit width of 8.0 nm. Inhibitor solutions in DMSO or buffer (50 mM Tris-HCl, 150 mM NaCl, 1 mM dithiothreitol, pH 8.5) were titrated into the enzyme in the same buffer. The concentration of enzyme in the direct binding measurements was 1 μM. Titration curves were corrected for inner filter effect from the chromophore, and the Kd values were calculated using the Scatchard equation (Grafit 4.0).

TABLE 2

Thermodynamic and Binding Data for Various TLMs

Kinetic and Thermodynamic parameters with MtbKasA

| Compound | Ki (μM) wt KasA | Slow Onset | C171Q KasA Ki (μM) | Ki* (μM) | $k_{on}$ (sec$^{-1}$) | $k_{off}$ (sec$^{-1}$) $T_r$, min |
|---|---|---|---|---|---|---|
| TLM | 226 ± 9 | Yes | 126 ± 16 | 2.2 ± 1.6 | 0.046 ± 0.002 | 0.0008 ± 0.0005 |
| TLM2 | 147 ± 2.2 | No | 46.9 ± 1 | | | |
| TLM3 | 330 ± 4 | Yes | 357 ± 35 | 7.1 ± 1.3 | 0.0166 ± 0.002 | 0.0004 ± 0.00001 (42) |
| TLM4 | 233 ± 7 | Yes | 305 ± 8 | 16 ± 2 | 0.0129 ± 0.002 | 0.0007 ± 0.00002 (24) |
| TLM5 | 150 ± 2.5 | No | 92.8 ± 1.4 | | | |
| TLM6 | 70.6 ± 1 | No | 69 ± 2 | | | |
| TLM7 | 68.2 ± 1 | No | 77.4 ± 1 | | | |
| TLM8 | 70.9 ± 0.6 | No | 82 ± 2 | | | |
| TLM9 | 10.8 ± 0.3 | No | 13.8 ± 0.2 | | | |
| TLM10 | 233.3 ± 7 | Yes | nd | | | |
| TLM26 | >200 | — | >130 | | | |
| TLM31 | 128 ± 4 | No | >400 | | | |
| TLM32 | | Yes | nd | | | |
| TLM33 | 274 ± 5 | No | >400 | | | |
| TLM34 | 25 ± 4 | No | 32 ± 3 | | | |
| TLM35 | 25.6 ± 0.5 | Yes | 8.2 ± 0.8 | 0.9 ± 0.2 | 0.035 ± 0.01 | 0.0039 ± 0.0003 (4.3) |
| TLM 36 | 21.8 ± 2.1 | Yes | 12.1 ± 0.6 | 0.46 ± 0.05 | 0.145 ± 0.03 | 0.0056 ± 0.0002 (2.9) |
| TLM37 | 31.4 ± 2 | No | 21.9 ± 2 | | | |
| TLM38 | 65.8 ± 2 | No | 65.2 ± 1.5 | | | |
| TLM39 | 34.3 ± 2 | No | 102 ± 3 | | | |
| TLM40 | >200 | No | >130 | | | |
| TLM41 | — | | — | | | |
| TLM42 | — | | — | | | |
| TLM43 | 65 ± 1 | No | 105 ± 4 | | | |
| TLM44 | Nd | | nd | | | |
| TLM45 | 26.4 ± 0.5 | No | 8.0 ± 0.5 | | | |

Example 7

TLM Analogue Activity Against Various Organisms

The MIC90 of various TLM analogs (Table 3) was determined against *M. tuberculosis* H37Rv, *M. smegmatis* MC$^2$155, *Y. pestis* A1122, *F. tularensis* LVS, *B. pseudomallei* Bp82z66, *B. thialandensis* Bt38 and *S. aureus* (RN4220 and BA1762) using reported protocol (47, 48).

TABLE 3

MIC90 of Various TLM Analogs

MIC (μg/ml)

| Compound | *M. smeg* | *M. tb* (MIC$_{99}$) | *F. tu* | *Y. pestis* | *B. thialandensis* Bt.38 (efflux$^-$) | *B. pseudomallei* | Staph. aureus RN4220 MSSA | Staph. aureus BAA1762 MRSA |
|---|---|---|---|---|---|---|---|---|
| TLM | 25 | 3.13 | 2.81 | 8.09 | | 13.12 | 75 | 75 |
| TLM2 | >100 | >100 | 123.93 | 250 | 148.296 | — | 150 | 100 |
| TLM3 | >100 | <7.8 | 6.902 | 144.6 | 148.296 | — | 150 | 125 |
| TLM4 | >100 | 12.5 | 25.84 | 250 | 250 | — | >200 | >200 |
| TLM5 | >100 | 25 | 3.451 | 250 | 250 | — | >64 | >100 |
| TLM6 | >100 | 25 | 3.153 | 250 | 250 | — | >64 | 75 |
| TLM7 | >100 | 25 | 1.731 | 250 | 81.044 | — | 64 | 50 |
| TLM8 | >100 | 25 | 2.17 | 250 | 125.893 | — | 32 | 50 |
| TLM9 | | 50 | 1.974 | 250 | 145.205 | — | 16 | 25 |
| TLM10 | | 12.5 | 23.486 | 250 | 250 | — | >64 | >100 |
| TLM26 | | >100 | 158.93 | | | 149.53 | >64 | >64 |
| TLM31 | | 25 | 3.095 | 250 | 250 | | 64 | 100 |
| TLM32 | | 50 | 15.341 | 250 | 250 | | >64 | >100 |
| TLM33 | >100 | 250 | 250 | 250 | | | >64 | >100 |
| TLM34 | | 12.5 | 250 | 250 | 250 | | >64 | >100 |

TABLE 3-continued

MIC90 of Various TLM Analogs

MIC (μg/ml)

| Compound | M. smeg | M. tb (MIC$_{99}$) | F. tu | Y. pestis | B. thialandensis Bt.38 (efflux⁻) | B. pseudomallei | Staph. aureus RN4220 MSSA | Staph. aureus BAA1762 MRSA |
|---|---|---|---|---|---|---|---|---|
| TLM35 | | 12.5 | 8.78 | | | 154.56 | 64 | 32 |
| TLM36 | | >100 | 98.11 | | | 159.8 | >64 | 64 |
| TLM37 | | 100 | 58.2 | | | 160.35 | >64 | >64 |
| TLM38 | | 12.5 | 1.82 | | | 171.41 | 16 | 32 |
| TLM39 | | >100 | 15.97 | | | 154.51 | 32 | 32 |
| TLM40 | | >100 | 39.14 | | | >256 | >64 | >64 |
| TLM41 | | >100 | 54.45 | | | >256 | >64 | >64 |
| TLM42 | | 100 | >256 | | | 177.95 | >64 | >64 |
| TLM43 | | >100 | 3.98 | | | 1.36 | 0.5 | 1 |
| TLM44 | | | | | | | 16 | 16 |
| TLM45 | | 50 | 0.21 | | | 4.58 | 0.5 | 2 |

DISCUSSION

Since the isolation of penicillin in 1940, the development of new antibacterial agents has included the optimization of natural products synthesized by microorganisms and plants (8). The bacterial fatty acid biosynthesis pathway (FAS-II) is a target for the development of novel antibacterial agents (1-3). While enoyl-ACP reductase (FabI) is the most heavily targeted FAS-II component for the development of novel antibacterials (3), the isolation of natural products (FIG. 1) that inhibit the FAS-II β-ketoacyl-ACP synthase (KAS) enzymes have demonstrated that the condensation step in fatty acid biosynthesis is also a promising target for drug discovery (2, 4-7).

TLM has a broad range of antibacterial activity, although with MIC values that are only in the range of 6-200 μg/ml (Table 4). Despite the relatively poor MIC values, TLM has activity in animal models of infection. This is partly the result of the favorable in vivo properties of the molecule, which satisfies all of the criteria in Lipinski's "Rule of 5" (13), as well as the low toxicity and high bioavailability of the molecule. The in vivo activity of TLM might also be partly due to the slow onset inhibition of the KAS enzymes in these organisms by this compound (15).

TABLE 4

MIC values for TLM

| Organism | MIC (μg/ml) |
|---|---|
| E. coli NIHJ | 200 |
| E. coli No9 | 100 |
| E. coli 11 | 25 |
| Shigella sonnei T1 | 100 |
| Shigella flexneri 2b T1 | 6.3 |
| Salmonella enterides T-1 | 12.5 |
| Salmonella typhi | 12.5 |
| Salmonella paratyphi | 50 |
| Serratia marcescens | 100 |
| Klebsiella pneumoniae | 100 |
| M. tuberculosis | 25 |
| Staphylococcus aureus | 25 |
| Pasteurella multocida | 0.2 |

Previous synthetic efforts have primarily explored modifications to the 5 position of the TLM thiolactone nucleus. NMR studies described in this invention demonstrate elaboration of the TLM 3 and 4 positions lead to an improvement their affinity for KAS enzymes. Importantly, this invention describes methods to facilitate the introduction of substituents at the 3 and 4 positions, TLM analogs generated through the use of these methods, and uses thereof.

Based on the structural studies described herein above in Example 1, elaboration of TLM at the 3 and/or 4 position results in compounds that have improved interaction with a TLM target. Thus, each TLM analogue of the present invention that is modified at the 3 and/or 4 position as compared to TLM will have an improved interaction with a target of TLM. Furthermore, because the compounds of the invention have an improved interaction with a target of TLM as exemplified in Example 6, an aspect of the invention provides a new class of antibiotics with an increased ability to inhibit the function of a target of TLM. Thus the compounds of the invention are antibiotics with increased antibiotic activity compared to TLM. An additional aspect of the invention provides novel synthetic methods and chemical intermediates that may be used to encompass chemical space about the thiolactone, including the synthesis of the 3 and 4 position TLM analogues described herein.

REFERENCES

1. Heath, R. J., and Rock, C. O. (2004) Fatty acid biosynthesis as a target for novel antibacterials, Curr. Opin. Investig. Drugs 5, 146-153.
2. Wright, H. T., and Reynolds, K. A. (2007) Antibacterial targets in fatty acid biosynthesis, Curr. Opin. Microbiol. 10, 447-453.
3. Lu, H., and Tonge, P. J. (2008) Inhibitors of FabI, an Enzyme Drug Target in the Bacterial Fatty Acid Biosynthesis Pathway, Acc. Chem. Res. 41, 11-20.
4. Oishi, H., Noto, T., Sasaki, H., Suzuki, K., Hayashi, T., Okazaki, H., Ando, K., and Sawada, M. (1982) Thiolactomycin, a new antibiotic. I. Taxonomy of the producing organism, fermentation and biological properties, J. Antibiot. 35, 391-395.
5. Nishida, I., Kawaguchi, A., and Yamada, M. (1986) Effect of thiolactomycin on the individual enzymes of the fatty acid synthase system in Escherichia coli, J. Biochem. 99, 1447-1454.
6. Price, A. C., Choi, K. H., Heath, R. J., Li, Z., White, S. W., and Rock, C. O. (2001) Inhibition of beta-ketoacyl-acyl carrier protein synthases by thiolactomycin and cerulenin. Structure and mechanism, J. Biol. Chem. 276, 6551-6559.

7. Wang, J., Soisson, S. M., Young, K., Shoop, W., Kodali, S., Galgoci, A., Painter, R., Parthasarathy, G., Tang, Y. S., Cummings, R., Ha, S., Dorso, K., Motyl, M., Jayasuriya, H., Ondeyka, J., Herath, K., Zhang, C., Hernandez, L., Allocco, J., Basilio, A., Tormo, J. R., Genilloud, O., Vicente, F., Pelaez, F., Colwell, L., Lee, S. H., Michael, B., Felcetto, T., Gill, C., Silver, L. L., Hermes, J. D., Bartizal, K., Barrett, J., Schmatz, D., Becker, J. W., Cully, D., and Singh, S. B. (2006) Platensimycin is a selective FabF inhibitor with potent antibiotic properties, Nature 441, 358-361.

8. Chain, E., Florey, H. W., Gardner, A. D., Heatley, N. G., Jennings, M. A., Orr-Ewing, J., and Sanders, A. G. (1940) Penicillin as a chemotherapeutic agent, Lancet 236, 226-228.

9. Nicolaou, K. C., Stepan, A. F., Lister, T., Li, A., Montero, A., Tria, G. S., Turner, C. I., Tang, Y., Wang, J., Denton, R. M., and Edmonds, D. J. (2008) Design, synthesis, and biological evaluation of platensimycin analogues with varying degrees of molecular complexity, J. Am. Chem. Soc. 130, 13110-13119.

10. Nicolaou, K. C., Edmonds, D. J., Li, A., and Tria, G. S. (2007) Asymmetric total syntheses of platensimycin, Angew Chem. Int. Ed. Engl. 46, 3942-3945.

11. Nicolaou, K. C., Li, A., and Edmonds, D. J. (2006) Total synthesis of platensimycin, Angew. Chem. Int. Ed. Engl. 45, 7086-7090.

12. Nomura, S., Horiuchi, T., Omura, S., and Hata, T. (1972) The action mechanism of cerulenin. I. Effect of cerulenin on sterol and fatty acid biosynthesis in yeast, J. Biochem. 71, 783-796.

13. Lipinski, C. A., Lombardo, F., Dominy, B. W., and Feeney, P. J. (2001) Experimental and computational approaches to estimate solubility and permeability in drug discovery and development settings, Adv. Drug Deliv. Rev. 46, 3-26.

14. Miyakawa, S., Suzuki, K., Noto, T., Harada, Y., and Okazaki, H. (1982) Thiolactomycin, a new antibiotic. IV. Biological properties and chemotherapeutic activity in mice, J. Antibiot. 35, 411-419.

15. Machutta, C. A., Bommineni, G. R., Luckner, S. R., Kapilashrami, K., Ruzsicska, B., Simmerling, C., Kisker, C., and Tonge, P. J. (2010) Slow onset inhibition of bacterial beta-ketoacyl-acyl carrier protein synthases by thiolactomycin, J. Biol. Chem. 285, 6161-6169.

16. Slayden, R. A., Lee, R. E., Armour, J. W., Cooper, A. M., Orme, I. M., Brennan, P. J., and Besra, G. S. (1996) Antimycobacterial action of thiolactomycin: an inhibitor of fatty acid and mycolic acid synthesis, Antimicrob. Agents Chemother. 40, 2813-2819.

17. Hayashi, T., Yamamoto, O., Sasaki, H., Kawaguchi, A., and Okazaki, H. (1983) Mechanism of action of the antibiotic thiolactomycin inhibition of fatty acid synthesis of *Escherichia coli*, Biochem. Biophys. Res. Commun. 115, 1108-1113.

18. Jackowski, S., Zhang, Y. M., Price, A. C., White, S. W., and Rock, C. 0. (2002) A missense mutation in the fabB (beta-ketoacyl-acyl carrier protein synthase I) gene confers thiolactomycin resistance to *Escherichia coli*, Antimicrob. Agents Chemother. 46, 1246-1252.

19. Tsay, J. T., Rock, C. O., and Jackowski, S. (1992) Overproduction of beta-ketoacyl-acyl carrier protein synthase I imparts thiolactomycin resistance to *Escherichia coli* K-12, J. Bacteriol. 174, 508-513.

20. Sakya, S. M., Suarez-Contreras, M., Dirlam, J. P., O'Connell, T. N., Hayashi, S. F., Santoro, S. L., Kamicker, B. J., George, D. M., and Ziegler, C. B. (2001) Synthesis and structure-activity relationships of thiotetronic acid analogues of thiolactomycin, Bioorg Med Chem Lett 11, 2751-2754.

21. Jones, S. M., Urch, J. E., Brun, R., Harwood, J. L., Berry, C., and Gilbert, I. H. (2004) Analogues of thiolactomycin as potential anti-malarial and anti-trypanosomal agents, Bioorg. Med. Chem. 12, 683-692.

22. Kim, P., Barry, C. E., and Dowd, C. S. (2006) Novel route to 5-position vinyl derivatives of thiolactomycin: Olefination vs. deformylation, Tetrahedron Lett. 47, 3447-3451.

23. Kim, P., Zhang, Y. M., Shenoy, G., Nguyen, Q. A., Boshoff, H. I., Manjunatha, U. H., Goodwin, M. B., Lonsdale, J., Price, A. C., Miller, D. J., Duncan, K., White, S. W., Rock, C. O., Barry, C. E., and Dowd, C. S. (2006) Structure-activity relationships at the 5-position of thiolactomycin: An intact (5R)-isoprene unit is required for activity against the condensing enzymes from *Mycobacterium tuberculosis* and *Escherichia coli*, J. Med. Chem. 49, 159-171.

24. Jones, A. L., Herbert, D., Rutter, A. J., Dancer, J. E., and Harwood, J. L. (2000) Novel inhibitors of the condensing enzymes of the type II fatty acid synthase of pea (*Pisum sativum*), Biochem. J. 347, 205-209.

25. Luckner, S. R., Machutta, C. A., Tonge, P. J., and Kisker, C. (2009) Crystal structures of *Mycobacterium tuberculosis* KasA show mode of action within cell wall biosynthesis and its inhibition by thiolactomycin, Structure 17, 1004-1013.

26. Lu, H., England, K., am Ende, C., Truglio, J. J., Luckner, S., Reddy, B. G., Marlenee, N. L., Knudson, S. E., Knudson, D. L., Bowen, R. A., Kisker, C., Slayden, R. A., and Tonge, P. J. (2009) Slow-onset inhibition of the FabI enoyl reductase from *francisella tularensis*: residence time and in vivo activity, ACS Chem. Biol. 4, 221-231.

27. Lu, H., and Tonge, P. J. (2010) Drug-target residence time: critical information for lead optimization, Curr. Opin. Chem. Biol. 14, 467-474.

28. Chen, J., Zhang, Z., Stebbins, J. L., Zhang, X., Hoffman, R., Moore, A., and Pellecchia, M. (2007) A fragment-based approach for the discovery of isoform-specific p38alpha inhibitors, ACS Chem. Biol. 2, 329-336.

29. Li, D., Levy, L. A., Gabel, S. A., Lebetkin, M. S., DeRose, E. F., Wall, M. J., Howell, E. E., and London, R. E. (2001) Interligand Overhauser effects in type II dihydrofolate reductase, Biochemistry 40, 4242-4252.

30. Becattini, B., and Pellecchia, M. (2006) SAR by ILOEs: an NMR-based approach to reverse chemical genetics, Chemistry 12, 2658-2662.

31. McFadden, J. M., Frehywot, G. L., and Townsend, C. A. (2002) A flexible route to (5R)-thiolactomycin, a naturally occurring inhibitor of fatty acid synthesis, Org. Lett. 4, 3859-3862.

32. McFadden, J. M., Medghalchi, S. M., Thupari, J. N., Pinn, M. L., Vadlamudi, A., Miller, K. I., Kuhajda, F. P., and Townsend, C. A. (2005) Application of a flexible synthesis of (5R)-thiolactomycin to develop new inhibitors of type I fatty acid synthase, J. Med. Chem. 48, 946-961.

33. Kamal, A., Azeeza, S., Malik, M. S., Shaik, A. A., and Rao, M. V. (2008) Efforts towards the development of new antitubercular agents: potential for thiolactomycin based compounds, J. Pharm. Pharm. Sci. 11, 56s-80s.

34. Stott, K.; Keeler, J.; Van, Q. N.; Shaka, A. J. J. Magn. Reson. 1997, 125, 302-324.

35. Stott, K.; Stonehouse, J.; Keeler, J.; Hwang, T.-L.; Shaka, A. J. J. Am Chem. Soc. 1995, 117, 4199-4200.

36. Hu, H.; Krishnamurthy, K. J. Magn. Reson. 2006, 182, 173-177.

37. Noto, T.; Miyakawa, S.; Oishi, H.; Endo, H.; Okazaki, H. J. Antibiot. (Tokyo) 1982, 35, 401-410.
38. Witkowski, A.; Joshi, A. K.; Lindqvist, Y.; Smith, S. Biochemistry 1999, 38, 11643-11650.
39. Sasaki, H.; Oishi, H.; Hayashi, T.; Matsuura, I.; Ando, K.; Sawada, M. J Antibiot. (Tokyo) 1982, 35, 396-400.
40. Brown, M. S.; Akopiants, K.; Resceck, D. M.; McArthur, H. A.; McCormick, E.; Reynolds, K. A. J. Am. Chem. Soc. 2003, 125, 10166-10167.
41. Becattini, B.; Culmsee, C.; Leone, M.; Zhai, D.; Zhang, X.; Crowell, K. J.; Rega, M. F.; Landshamer, S.; Reed, J. C.; Plesnila, N.; Pellecchia, M. Proc. Natl. Acad. Sci. USA 2006, 103, 12602-12606.
42. Edzes, H. T.; Samulski, E. T. Nature 1977, 265, 521-523.
43. Delano, W. L. www.pymol.org 2002
44. Szabo A.; Kunzle N.; Mallat T.; Baiker A. Tetrahedron: Asymmetry 1999, 10, 61-76
45. Spry C.; Chai C. L. L.; Kirk K.; Kaliba K. J. Antimicrob. Agents Chemother 2005, 49, 4649-4657
46. Marion, D.; Ikura, M.; Tschudin, R.; Bax, A. J. Magn. Reson. 1989, 85, 393-399.
47. Sullivan, T. J., Truglio, J. J., Boyne, M. E., Novichenok, P., Zhang, X., Stratton, C. F., Li, H. J., Kaur, T., Amin, A., Johnson, F., Slayden, R. A., Kisker, C., and Tonge, P. J. ACS Chemical Biology (2006) 1, 43-53.
48. Lu, H., England, K., am Ende, C., Truglio, J. J., Luckner, S., Reddy, B. G., Marlenee, N. L., Knudson, S. E., Knudson, D. L., Bowen, R. A., Kisker, C., Slayden, R. A., and Tonge, P. J. ACS Chemical Biology (2009) 4, 221-231.

What is claimed is:

1. A compound having the structure

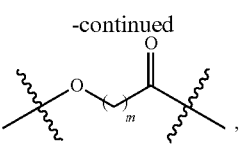

wherein $R_1$ is H,

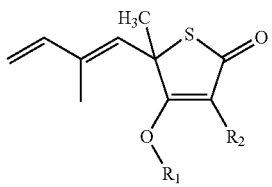

wherein
n and q are independently an integer from 0 to 8;
A is absent or present and when present is

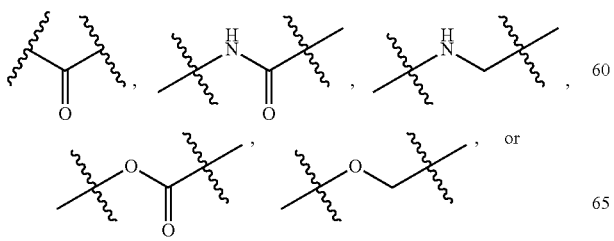

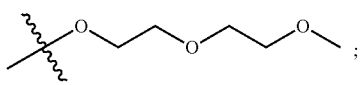

wherein m is an integer from 0 to 8;
$R_3$ is an amino, alkyl, aryl, heteroaryl, diol, piperazine, morpholine, piperidine, triazole, azide or biphenyl, each with or without substitution, branched or unbranched, or

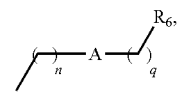

and
$R_4$ is alkyl, aryl, or heteroaryl, each with or without substitution, branched or unbranched,
$R_2$ is H, alkyl, aryl, heteroaryl, pyrrole, diazole, or triazole, each with or without substitution, or

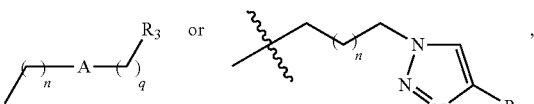

wherein
n and q are independently an integer from 0 to 8;
A is present and when present is

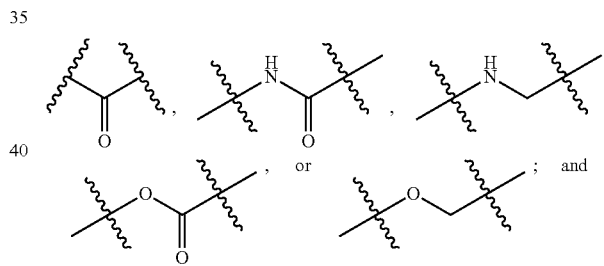

$R_6$ is azide, methoxy, trifluoromethyl, biphenyl, substituted phenyl, substituted triazole, or alkyl, aryl or heteroaryl, with or without substitution, branched or unbranched, or
A is absent; and
$R_6$ is azide, methoxy, trifluoromethyl, biphenyl, substituted phenyl, substituted triazole, aryl or heteroaryl,
when $R_1$ is H then $R_2$ is other than H, and when $R_2$ is H, then $R_1$ is other than H,
or a pharmaceutically acceptable salt thereof.

2. A compound having the structure

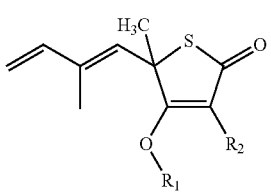

wherein R₁ is

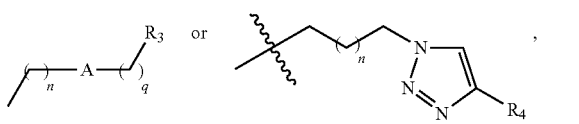

wherein
n and q are independently an integer from 0 to 8;
A is absent or present and when present is

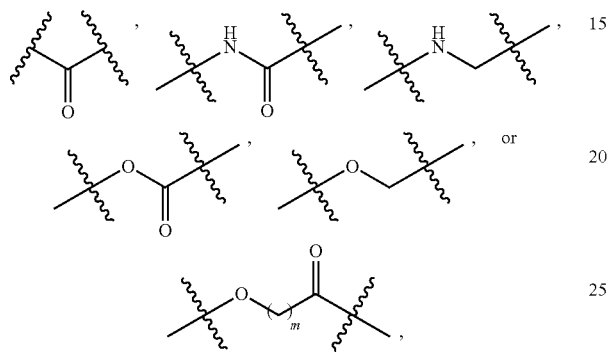

wherein m is an integer from 0 to 8;
R₃ is an amino, aryl, heteroaryl, diol, piperazine, morpholine, piperidine, triazole, azide or biphenyl, each with or without substitution, or

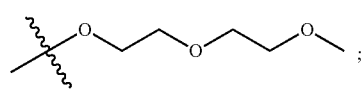 [SMILES: *OCCOCCOC]

and
R₄ is alkyl, aryl, or heteroaryl, each with or without substitution, branched or unbranched,
R₂ is H, CH₃, or alkyl, aryl, heteroaryl, pyrrole, diazole, or triazole, each with or without substitution, branched or unbranched, or

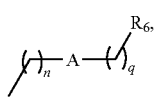

wherein
n and q are independently an integer from 0 to 8;
A is absent or present and when present is

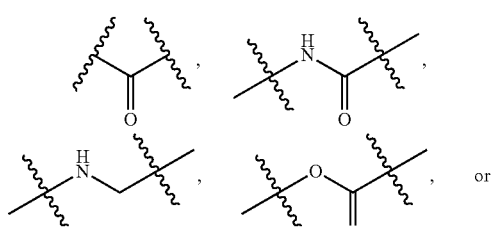

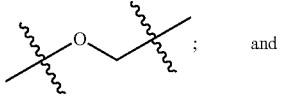

R₆ is azide, methoxy, trifluoromethyl, biphenyl, substituted phenyl, substituted triazole, or alkyl, aryl or heteroaryl, with or without substitution, branched or unbranched,
or a pharmaceutically acceptable salt thereof.

3. A compound having the structure

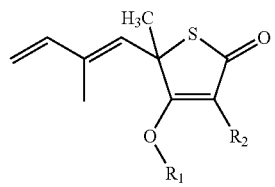

wherein R₁ is H,

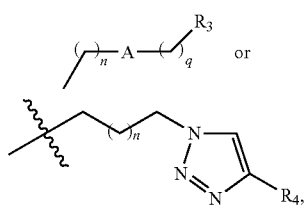

wherein
n and q are independently an integer from 0 to 8;
A is

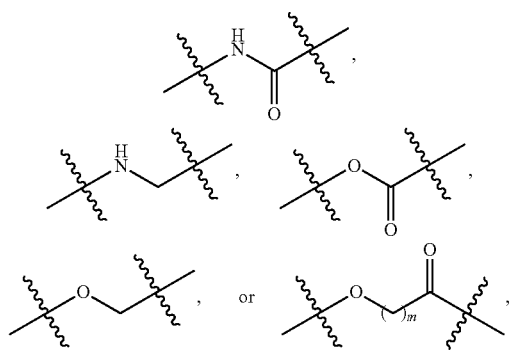

wherein m is an integer from 0 to 8;
R₃ is alkyl, aryl, heteroaryl, diol, piperazine, morpholine, piperidine, or biphenyl, each with or without substitution, branched or unbranched, or

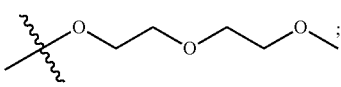 [SMILES: *OCCOCCOC]

and
R₄ is alkyl, aryl, or heteroaryl, each with or without substitution, branched or unbranched, $R_2$ is H, $CH_3$, aryl, heteroaryl, pyrrole, diazole, or triazole, each with or without substitution, or

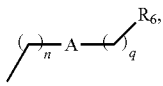

wherein
n and q are independently an integer from 0 to 8;
A is

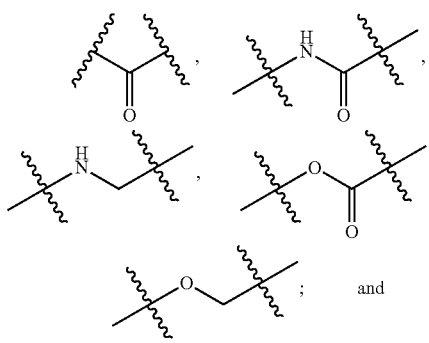

$R_6$ is alkyl, aryl or heteroaryl, with or without substitution, branched or unbranched, or
when $R_1$ is H then $R_2$ is other than H or $CH_3$, and when $R_2$ is H or $CH_3$ then $R_1$ is other than H,
or a pharmaceutically acceptable salt thereof.

4. A compound having the structure

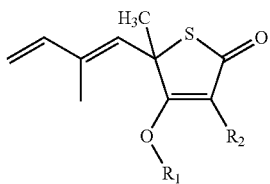

wherein $R_1$ is

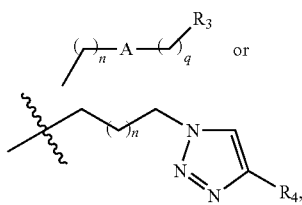

wherein
n and q are independently an integer from 0 to 8;
A is

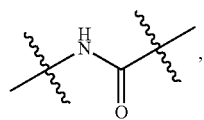

-continued

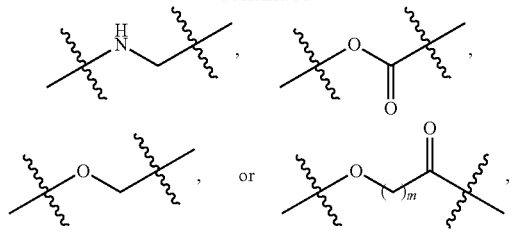

wherein m is an integer from 0 to 8;
$R_3$ is alkyl, aryl, heteroaryl, diol, piperazine, morpholine, piperidine, or biphenyl, each with or without substitution, branched or unbranched, or

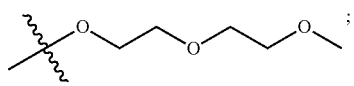 [SMILES: *OCCOCCOC]

and
$R_4$ is alkyl, aryl, or heteroaryl, each with or without substitution, branched or unbranched,
$R_2$ is H, $CH_3$, or alkyl, aryl, heteroaryl, pyrrole, diazole, or triazole, each with or without substitution, branched or unbranched, or

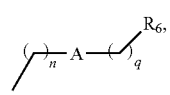

wherein
n and q are independently an integer from 0 to 8;
A is

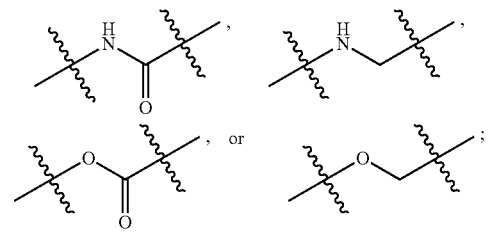

and
$R_6$ is alkyl, aryl or heteroaryl, with or without substitution, branched or unbranched,
or a pharmaceutically acceptable salt thereof.

5. The compound of claim 4 wherein $R_1$ is

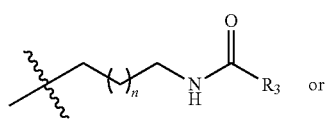

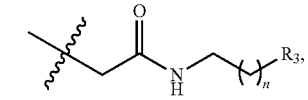

wherein n and q are independently an integer from 0 to 8; and $R_3$ is alkyl, aryl, heteroaryl, diol, piperazine, morpholine, piperidine, or biphenyl, each with or without substitution, branched or unbranched;

or a pharmaceutically acceptable salt thereof.

6. The compound of claim 5 wherein $R_3$ is

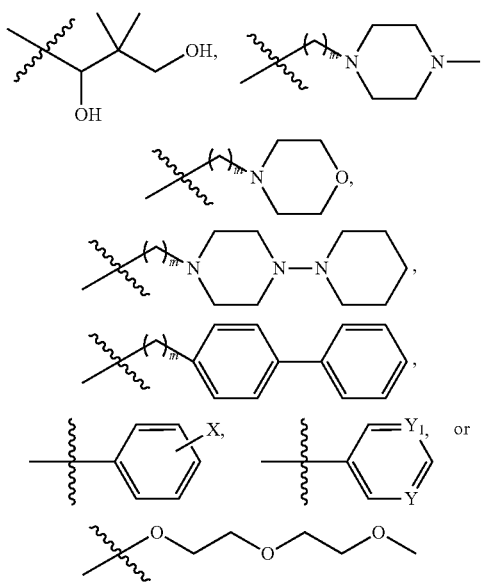

wherein m is an integer from 0-8;

X is F, Cl, Br, phenyl, or $C_1$-$C_4$ alkyl;

Y is N or C; and $Y_1$ is N or C, or a pharmaceutically acceptable salt thereof.

7. The compound of claim 6 having the structure

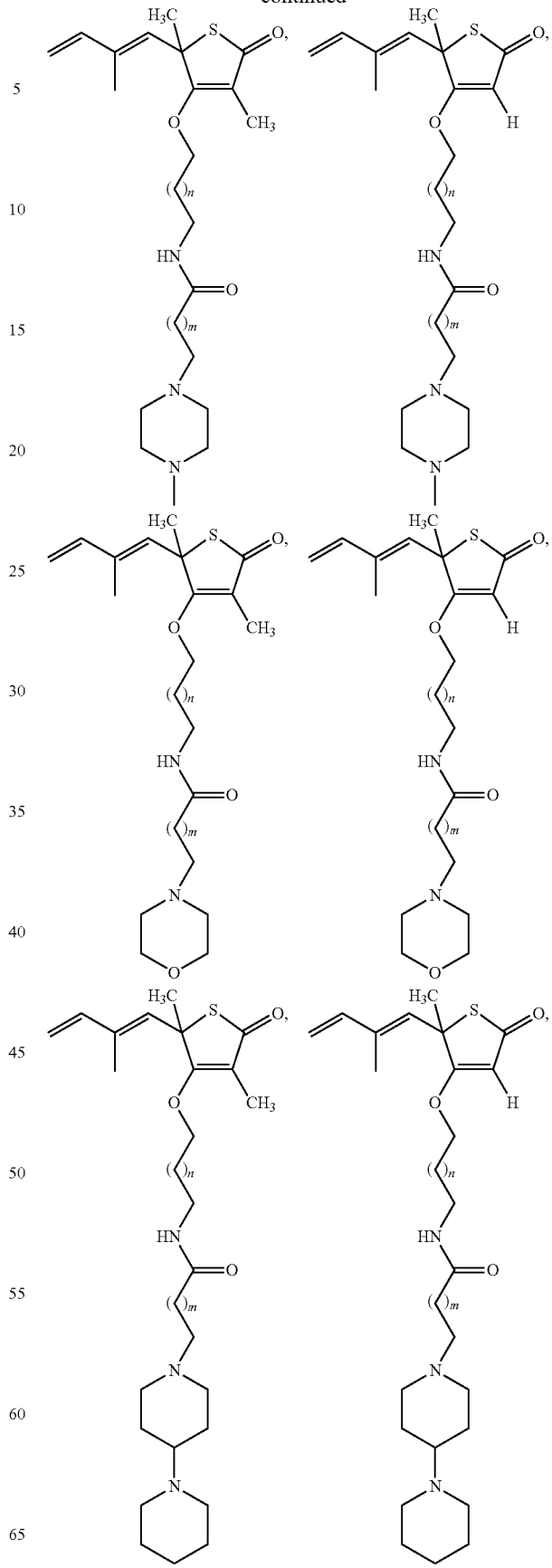

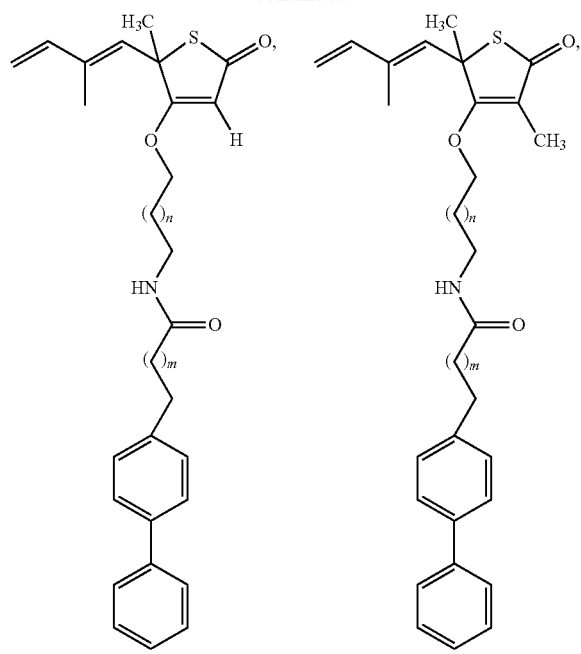

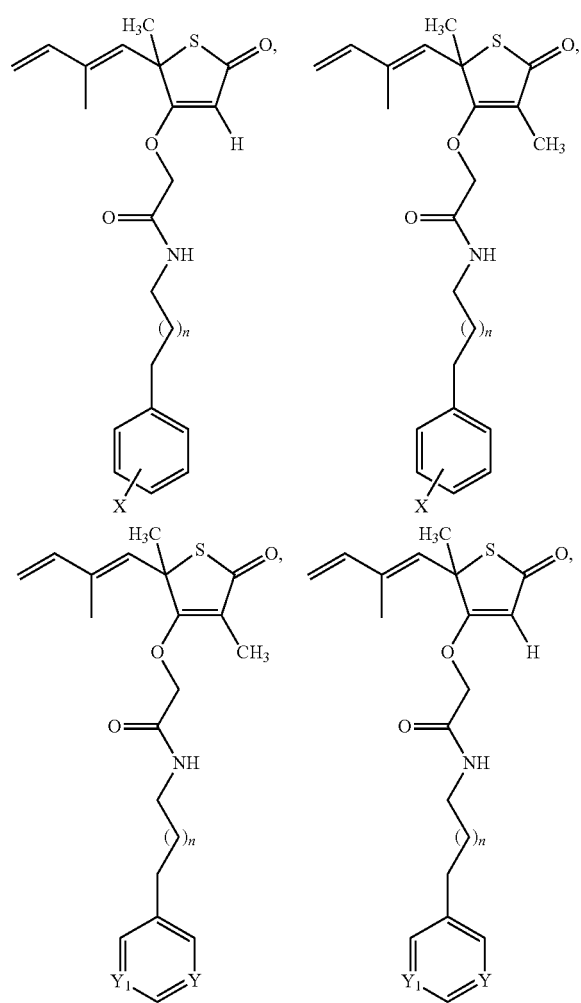

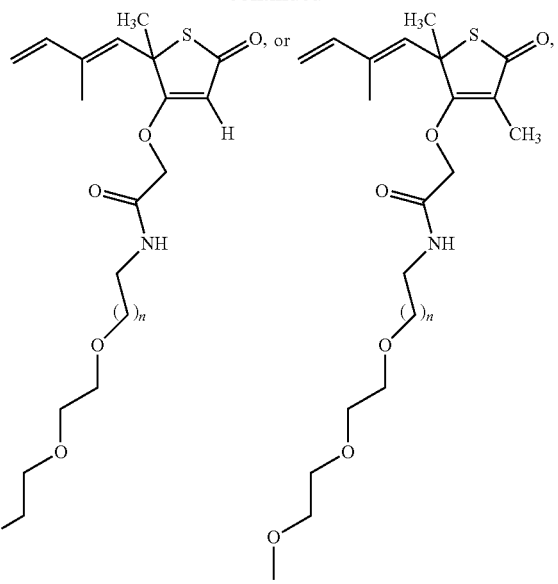

wherein n and m are each independently an integer from 0 to 8;

X is F, Cl, Br, phenyl, or $C_1$-$C_4$ alkyl;

Y is N or C; and $Y_1$ is N or C, or a pharmaceutically acceptable salt thereof.

8. The compound of claim 4, wherein $R_1$ is

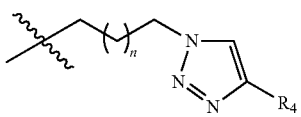

wherein n is an integer from 0 to 8; and $R_4$ is alkyl, aryl, or heteroaryl, each with or without substitution, branched or unbranched, or a pharmaceutically acceptable salt thereof.

9. The compound of claim 8 having the structure

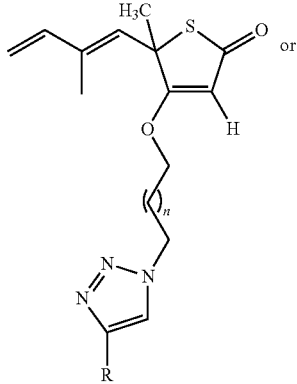

-continued

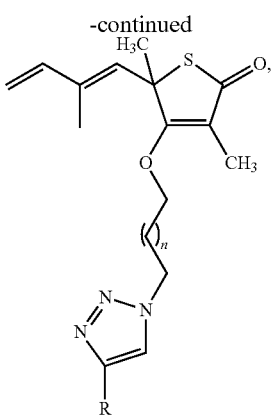

wherein
n is an integer from 0 to 8; and
R₄ is alkyl, aryl, or heteroaryl, each with or without substitution, branched or unbranched,
or a pharmaceutically acceptable salt thereof.

10. The compound of claim 1 wherein R₂ is

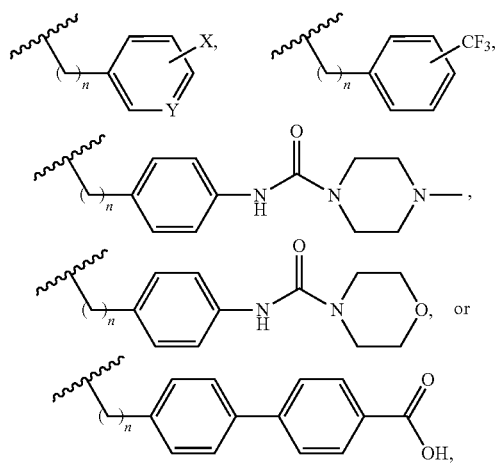

wherein
n is an integer from 0-8;
X is H, Cl, F, Br, phenyl, $CO_2H$, or aryl or $C_1$-$C_4$ alkyl each with or without substitution, branched or unbranched; and
Y is C, O, S, or N,
or a pharmaceutically acceptable salt thereof.

11. The compound of claim 2 wherein R₂ is

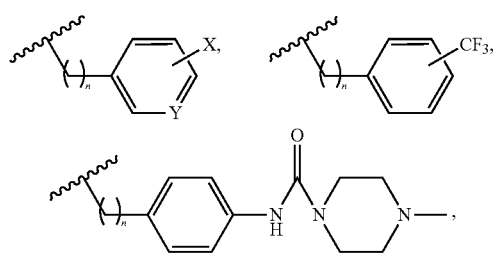

-continued

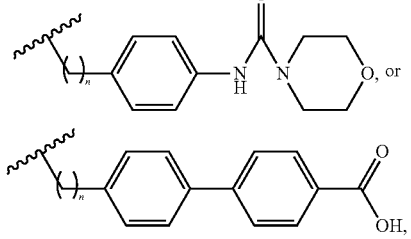

wherein
n is an integer from 0-8;
X is H, Cl, F, Br, phenyl, $CO_2H$, or aryl or $C_1$-$C_4$ alkyl each with or without substitution, branched or unbranched; and
Y is C, O, S, or N,
or a pharmaceutically acceptable salt thereof.

12. The compound of claim 3 having the structure

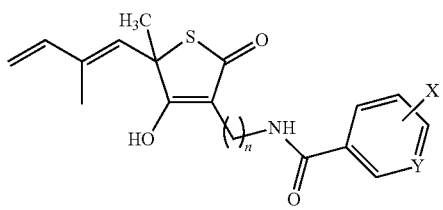

wherein n is an integer from 0-8;
X is F, Cl, Br, phenyl, or $CO_2H$; and
Y is N or C,
or a pharmaceutically acceptable salt thereof.

13. The compound of claim 3 having the structure

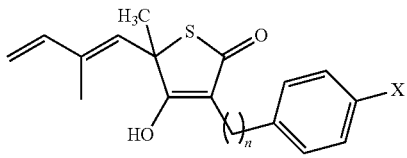

wherein n is an integer from 0-8;
X is F, Cl, Br, phenyl, or $CO_2H$; and
Y is N or C,
or a pharmaceutically acceptable salt thereof.

14. The compound of claim 10 having the structure

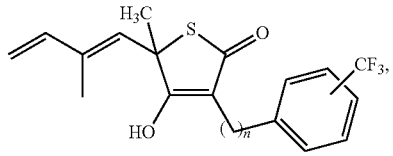

-continued

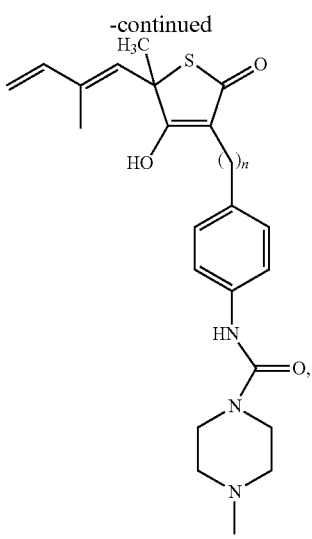

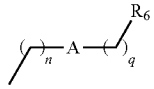

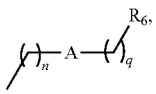

wherein n is an integer from 0 to 8,
or a pharmaceutically acceptable salt thereof.

15. The compound of claim 3 wherein $R_2$ is

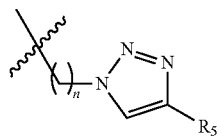

wherein
n is an integer from 0-8; and
$R_5$ is alkyl, aryl, or heteroaryl, each with or without substitution, branched or unbranched,
or a pharmaceutically acceptable salt thereof.

16. The compound of claim 15 having the structure

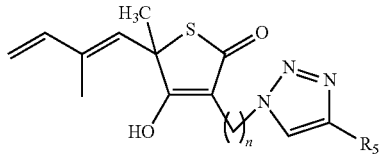

wherein
n is an integer from 0-8; and
$R_5$ is alkyl, aryl, or heteroaryl, each with or without substitution, branched or unbranched,
or a pharmaceutically acceptable salt thereof.

17. The compound of claim 3 wherein $R_2$ is

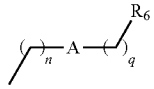

wherein
n and q are independently an integer from 0 to 8;
A is

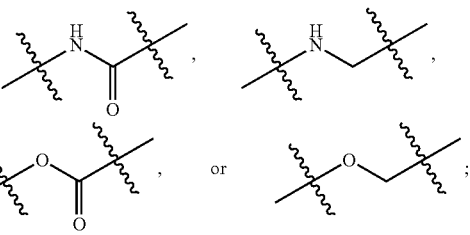

and
$R_6$ is alkyl, aryl or heteroaryl, with or without substitution, branched or unbranched,
or a pharmaceutically acceptable salt thereof.

18. The compound of claim 4 wherein $R_2$ is

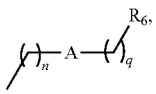

wherein
n and q are independently an integer from 0 to 8;
A is

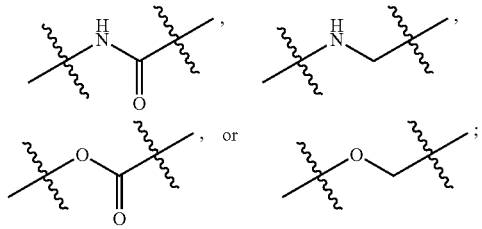

and
R$_6$ is alkyl, aryl or heteroaryl, with or without substitution, branched or unbranched,
or a pharmaceutically acceptable salt thereof.

19. The compound of claim 17 having the structure

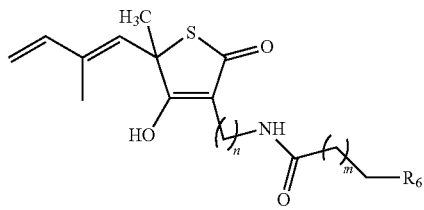

wherein
n and m are each independently an integer from 0 to 8;
and R$_6$ is alkyl, aryl or heteroaryl, each with or without substitution, branched or unbranched,
or a pharmaceutically acceptable salt thereof.

20. The compound of claim 19 wherein R$_6$ is

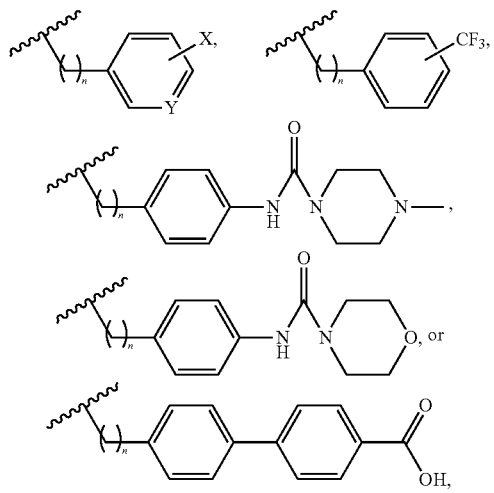

wherein
n is an integer from 0-8;
X is H, Cl, F, Br, phenyl, CO$_2$H, or aryl or C$_1$-C$_4$ alkyl each with or without substitution, branched or unbranched; and
Y is C, O, S, or N,
or a pharmaceutically acceptable salt thereof.

21. The compound of claim 1 wherein R$_1$ is

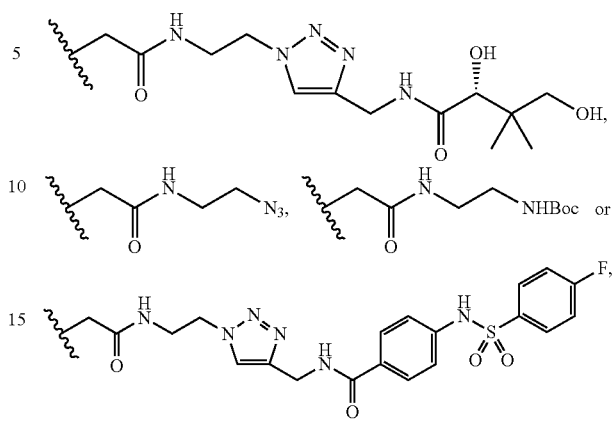

or a pharmaceutically acceptable salt thereof.

22. The compound of claim 2 wherein R$_1$ is

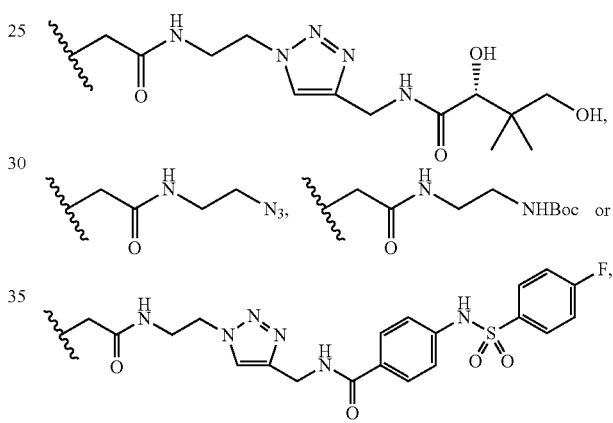

or a pharmaceutically acceptable salt thereof.

23. The compound of claim 1 wherein R$_2$ is

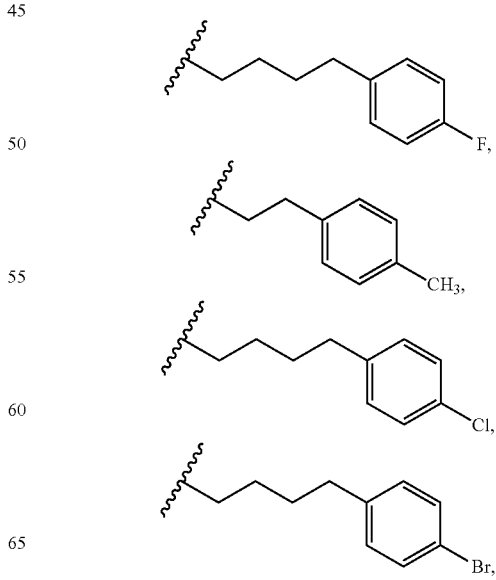

71
-continued
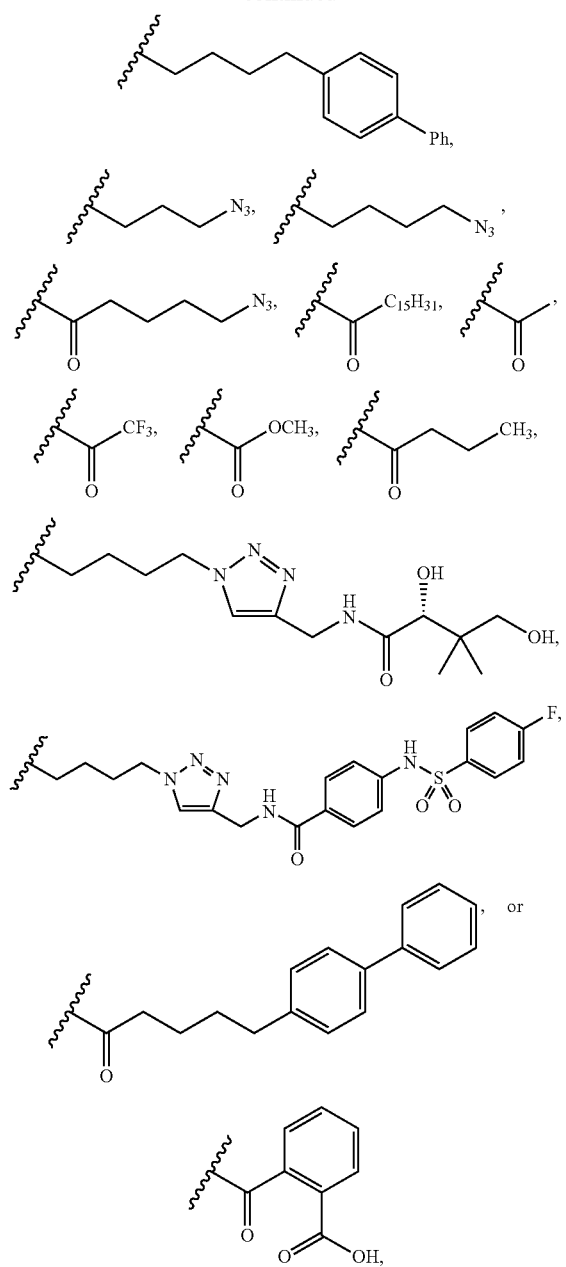
or a pharmaceutically acceptable salt thereof.
24. The compound of claim 2 wherein $R_2$ is
72
-continued
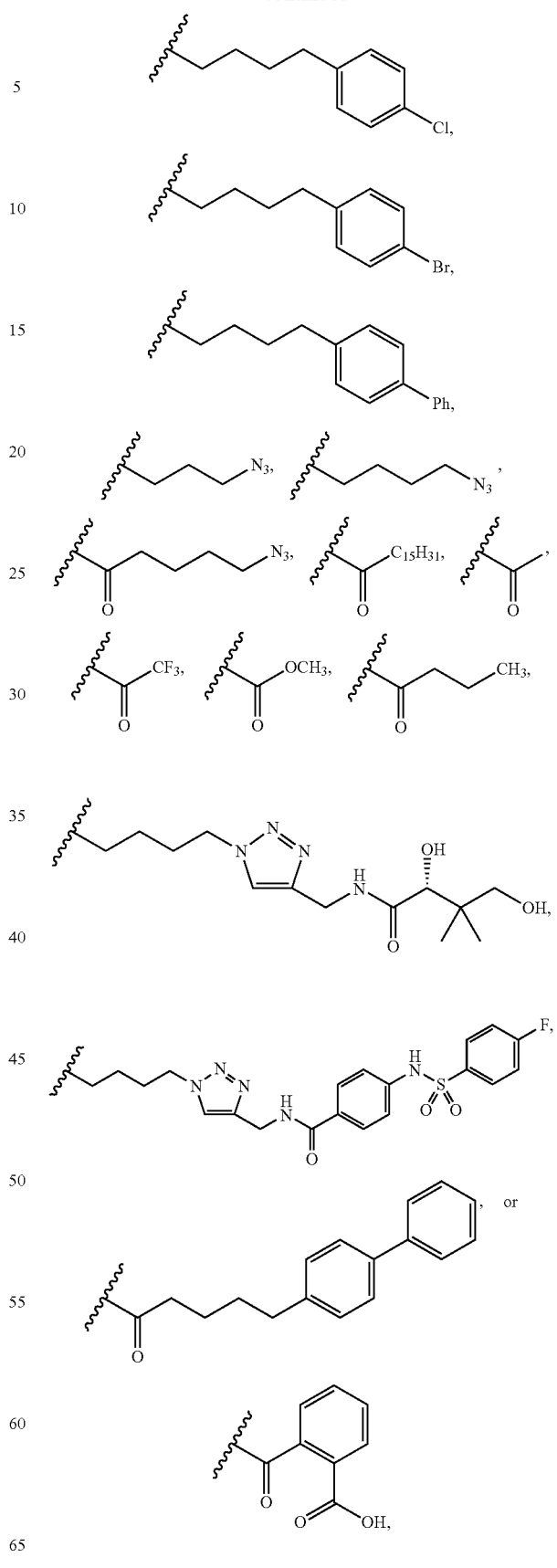
or a pharmaceutically acceptable salt thereof.

25. The compound of claim 1 having the structure
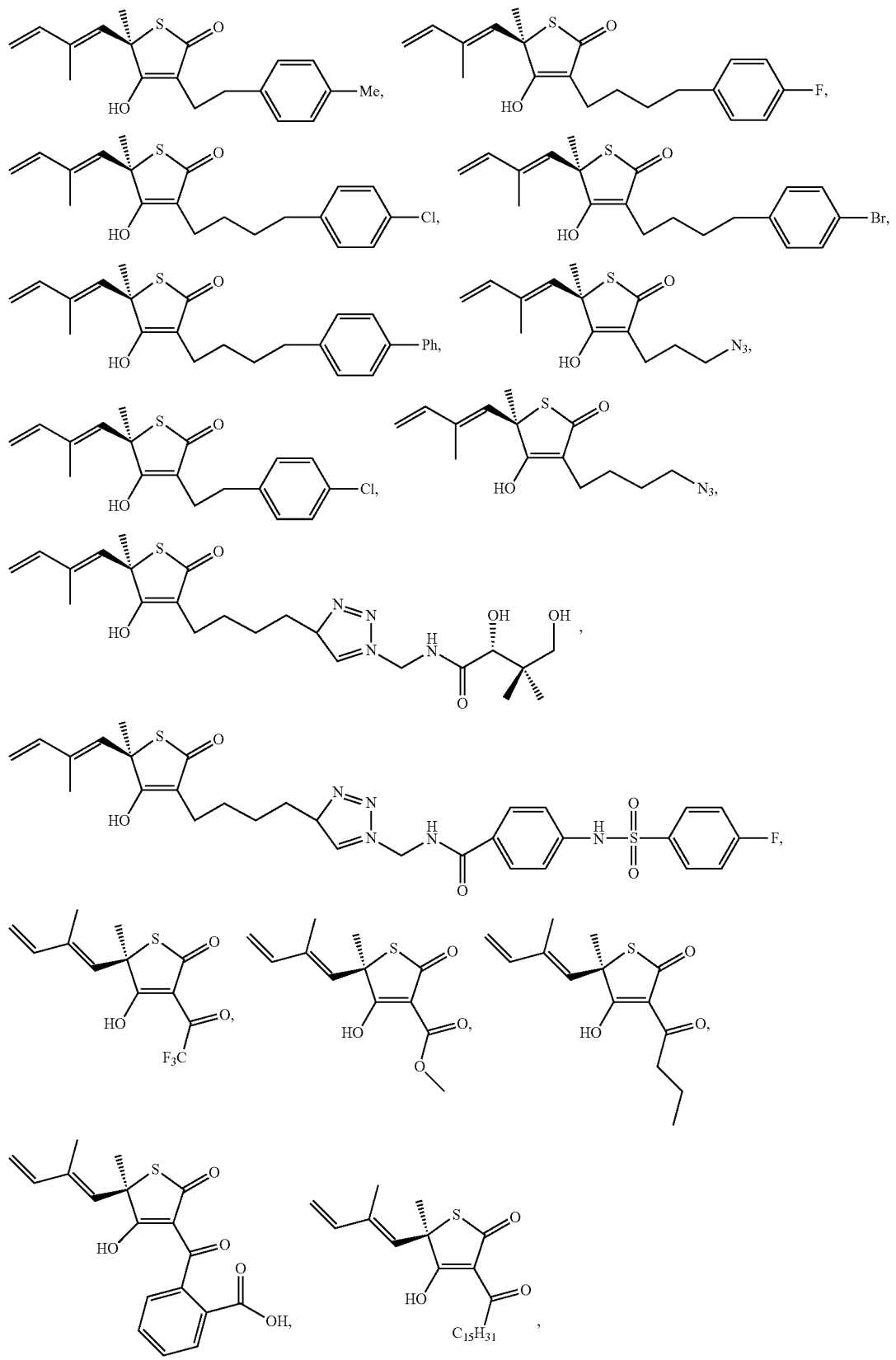

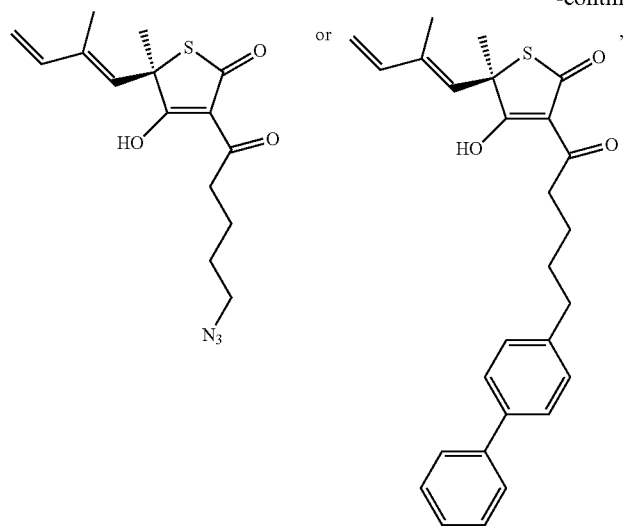
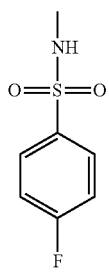
or a pharmaceutically acceptable salt thereof.
26. The compound of claim 1 having the structure
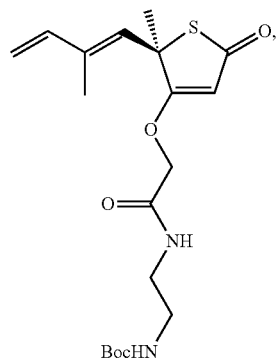
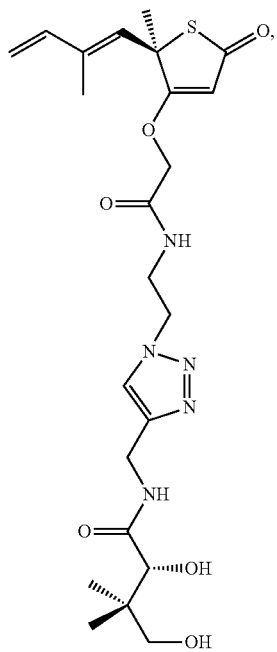

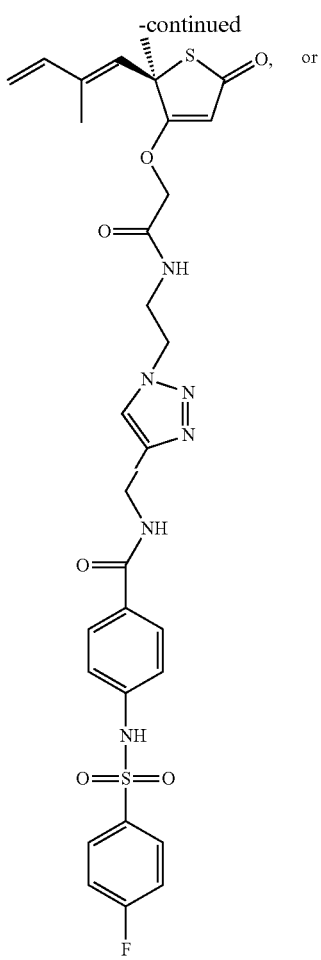

or a pharmaceutically acceptable salt thereof.

27. The compound of claim 3 having the structure

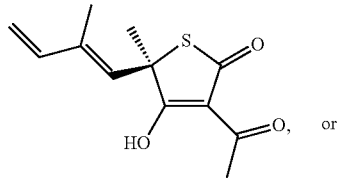 [SMILES: C=C/C(C)=C/[C@@]1(C)SC(=O)C(C(C)=O)=C1O ; "or"]

or a pharmaceutically acceptable salt thereof.

28. A pharmaceutical composition comprising the compound of claim 1 and a pharmaceutically acceptable carrier.

29. A pharmaceutical composition comprising the compound of claim 2 and a pharmaceutically acceptable carrier.

30. A pharmaceutical composition comprising the compound of claim 3 and a pharmaceutically acceptable carrier.

31. A pharmaceutical composition comprising the compound of claim 4 and a pharmaceutically acceptable carrier.

* * * * *